US012472367B2

(12) United States Patent
Vandenburg et al.

(10) Patent No.: US 12,472,367 B2
(45) **Date of Patent: *Nov. 18, 2025**

(54) STRAIN RELIEF SYSTEMS FOR ACTIVE IMPLANTABLE MEDICAL DEVICES

(71) Applicant: NeuroPace, Inc., Mountain View, CA (US)

(72) Inventors: Joseph Vandenburg, Sunnyvale, CA (US); Jerzy A. Sochor, Sunnyvale, CA (US)

(73) Assignee: NeuroPace, Inc., Mountain View, CA (US)

( * ) Notice: Subject to any disclaimer, the term of this patent is extended or adjusted under 35 U.S.C. 154(b) by 258 days.

This patent is subject to a terminal disclaimer.

(21) Appl. No.: 18/196,688

(22) Filed: May 12, 2023

(65) Prior Publication Data

US 2023/0277858 A1 Sep. 7, 2023

Related U.S. Application Data

(63) Continuation of application No. 16/691,384, filed on Nov. 21, 2019, now Pat. No. 11,684,788.

(60) Provisional application No. 62/773,116, filed on Nov. 29, 2018.

(51) Int. Cl.

| | |
|---|---|
| ***A61N 1/375*** | (2006.01) |
| ***H01R 13/52*** | (2006.01) |
| ***H01R 13/58*** | (2006.01) |

(52) U.S. Cl.

CPC ..... *A61N 1/37514* (2017.08); *H01R 13/5213* (2013.01); *H01R 13/5224* (2013.01); *H01R 13/582* (2013.01)

(58) Field of Classification Search

CPC ............ A61N 1/37514; H01R 13/5213; H01R 13/5224; H01R 13/582

See application file for complete search history.

(56) References Cited

U.S. PATENT DOCUMENTS

| | | | | |
|---|---|---|---|---|
| 6,810,285 | B2 | 10/2004 | Pless et al. | |
| 11,684,788 | B2 * | 6/2023 | Vandenburg ......... | H01R 13/582 607/116 |
| 2008/0140149 | A1 | 6/2008 | John et al. | |
| 2017/0151438 | A1 | 6/2017 | Orinski | |

* cited by examiner

*Primary Examiner* — Lindsey G Wehrheim

(74) *Attorney, Agent, or Firm* — LOZA & LOZA, LLP; David S. Sarisky

(57) ABSTRACT

A device for implant in a hole in cranium relative to a bone table includes a can having an electrical-contact pad. The can has a perimeter edge defining a boundary, and a recessed portion with an upper surface positioned to lie beneath the bone table when the can is placed in the hole. The device also include a cover assembly that couples to and decouples from the can at the electrical-contact pad. A strain relief system includes a lower strain relief and an upper strain relief. The lower strain relief defines channels that receive a portion of a lead and includes a curved portion that extends upward from the upper surface of the recessed portion to the bone table, and a linear portion that extends from the curved portion to an end beyond the perimeter edge. The upper strain relief couples to and decouples from the can and/or the lower strain relief.

16 Claims, 23 Drawing Sheets

FIG. 6D
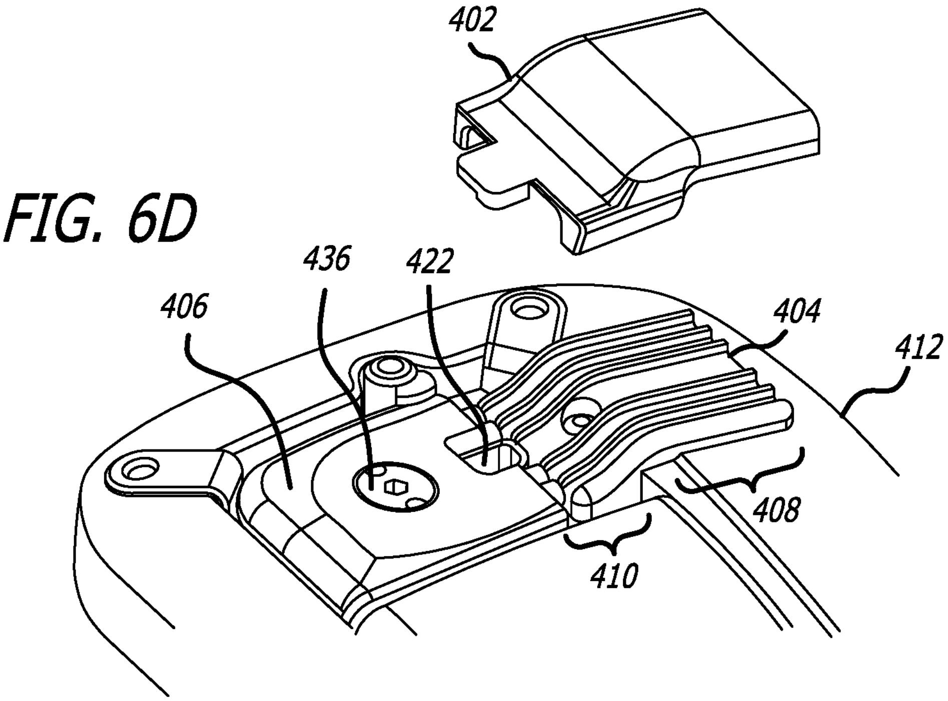
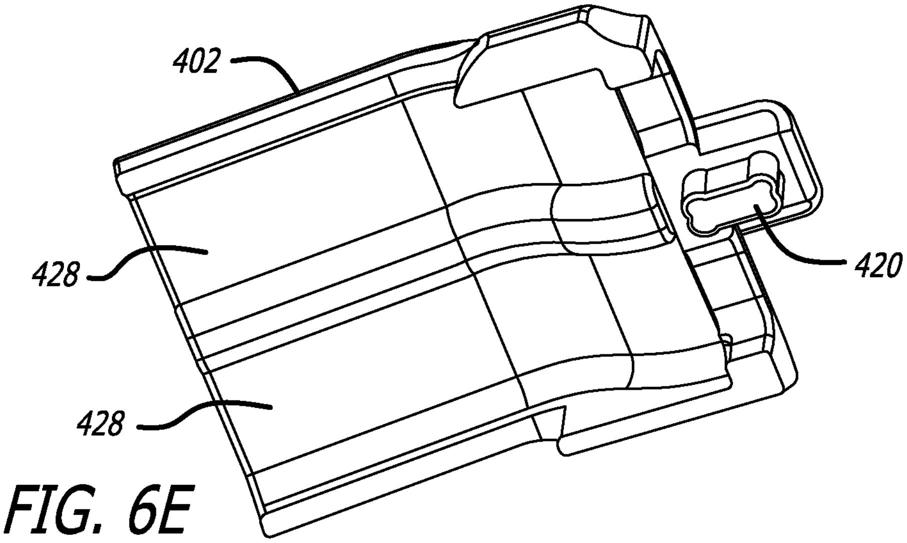
FIG. 6E

FIG. 7A
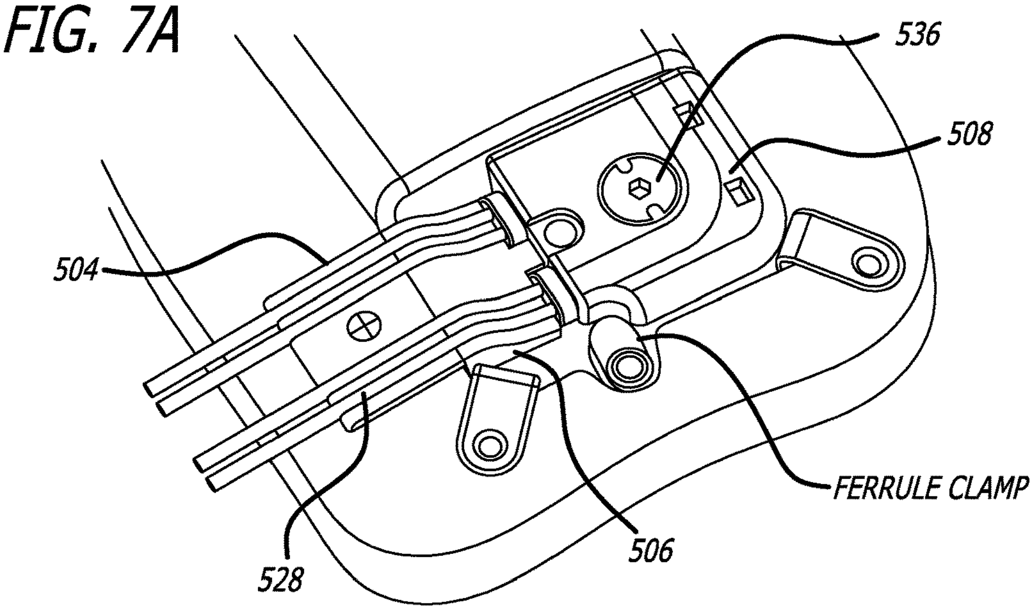
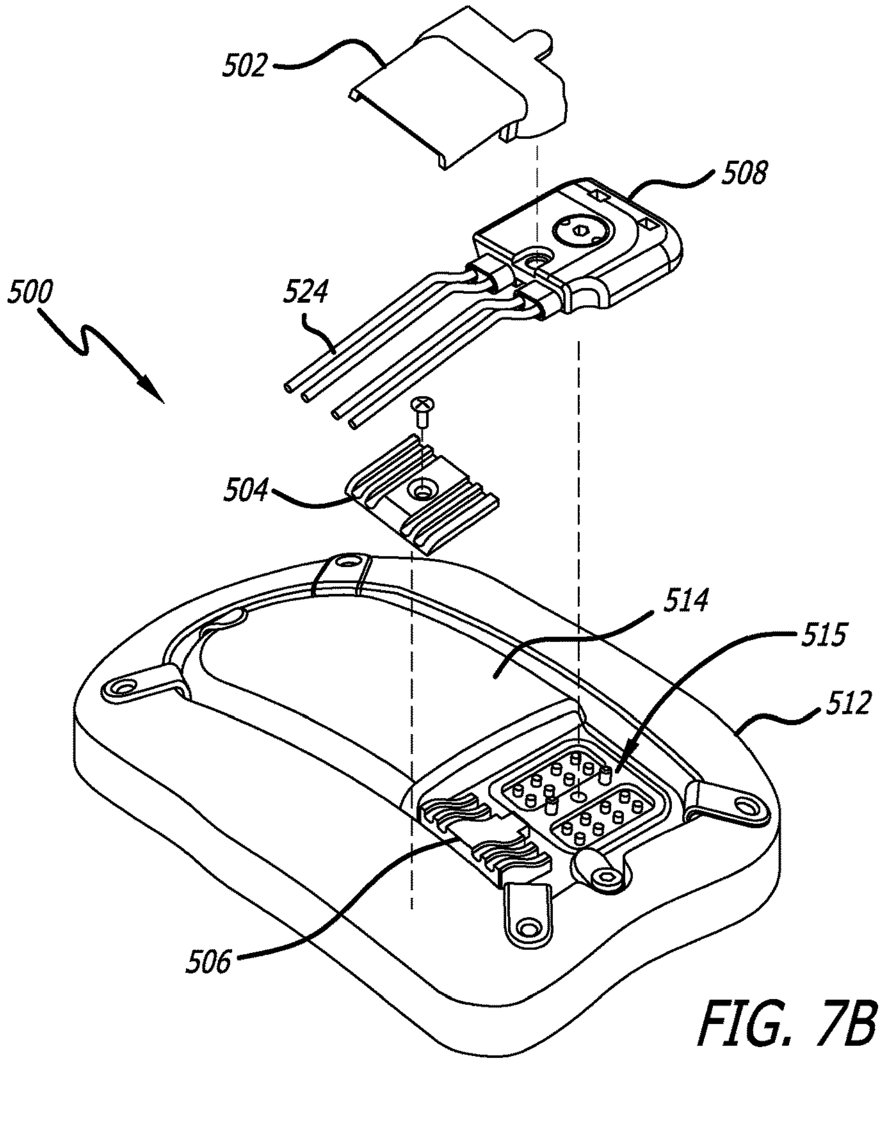
FIG. 7B

FIG. 8A
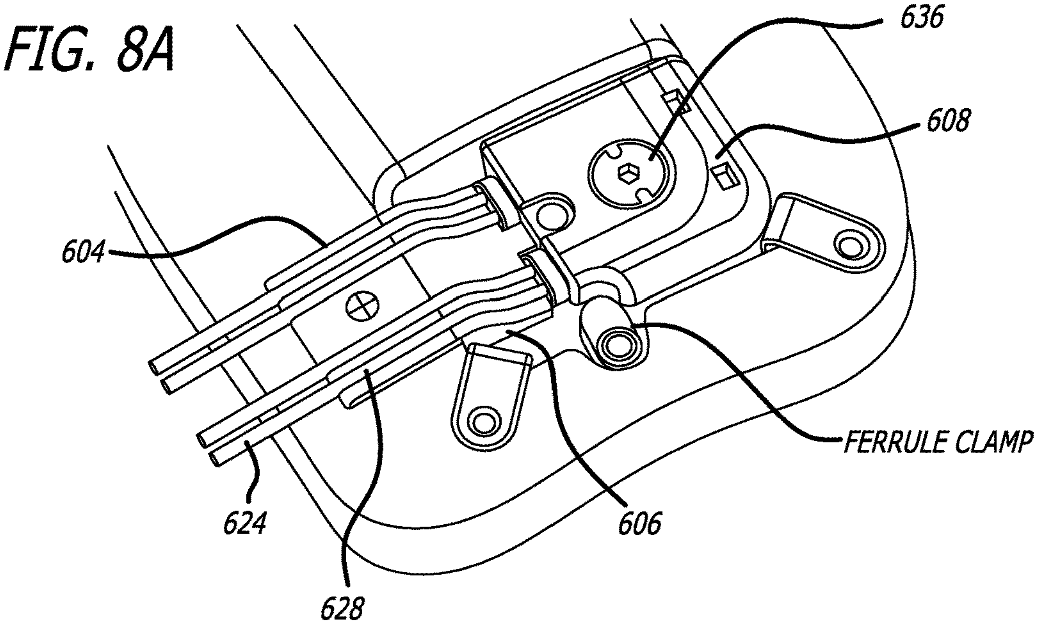
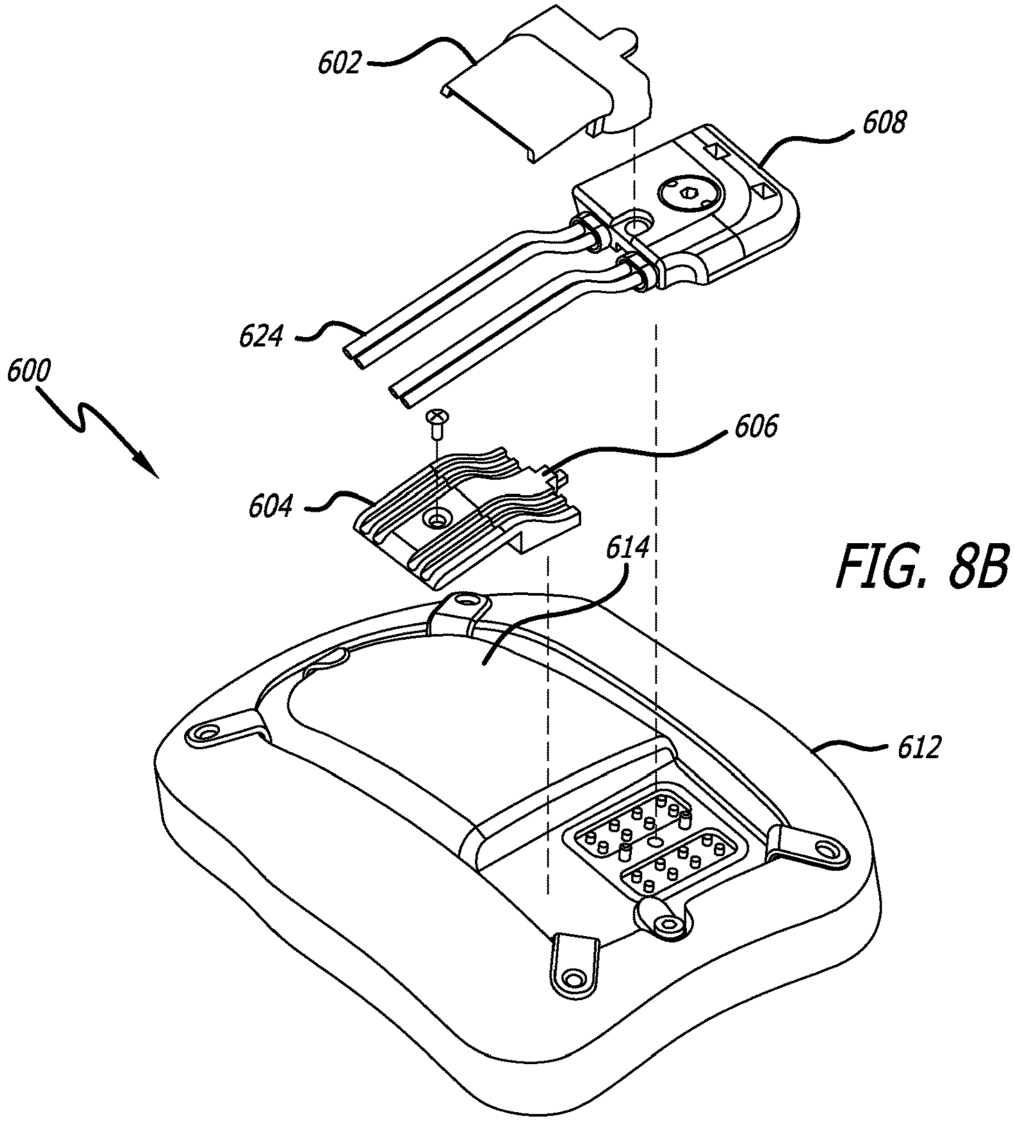
FIG. 8B

STRAIN RELIEF SYSTEMS FOR ACTIVE IMPLANTABLE MEDICAL DEVICES

CROSS-REFERENCE TO RELATED APPLICATIONS

This application is a continuation of U.S. application Ser. No. 16/691,384, filed on Nov. 21, 2019, entitled "Strain Relief Systems For Active Implantable Medical Devices," now U.S. Pat. No. 11,684,788, which claims the benefit of and priority to U.S. Provisional Patent Application Ser. No. 62/773,116, filed Nov. 29, 2018, for "Strain Relief Systems For Active Implantable Medical Devices," the entire disclosures of which are incorporated herein by reference.

TECHNICAL FIELD

The present disclosure relates generally to strain reliefs for medical devices, and more particularly, to strain relief systems for leads coupled to active implantable medical devices.

BACKGROUND

Some implantable medical device systems, such as described in U.S. Pat. No. 6,810,285 to Pless et al. for "Seizure Sensing and Detection Using An Implantable Device," include a medical device, e.g., neurostimulator, that is implanted in a patient's cranium. For example, with reference to FIG. 1A, a neurostimulator and leads of a responsive neurostimulation system are shown schematically, implanted in a patient. To implant the neurostimulator, a surgeon cuts a craniectomy hole using a template that approximates the shape of the neurostimulator. The surgeon fits a tray or ferrule into the hole and attaches or otherwise secures it to the cranium, for example, using bone screws and/or folding tabs providing on the tray. The surgeon then situates the neurostimulator into the tray ferrule.

To implant a lead, the surgeon needs access to the brain. A surgeon may gain access to the brain for purposes of implanting a lead by creating an opening through the skull. A opening may be created by drilling a hole through the skull, by performing a craniotomy (temporarily removing a bone flap from the skull and replacing the flap after access to the brain is no longer needed).

In FIG. 1A, a burr hole is formed for purposes of implanting a depth lead and a hole or fissure like opening at an edge of the craniotomy is formed for purposes of implanting a cortical strip lead. A distal portion of the depth lead extends into the patient's brain tissue from the burr hole, and a proximal portion extends proximally from the burr hole onto a top surface of the cranium to connect to the neurostimulator. The top surface is referred to herein as the bone table. A distal portion of a cortical strip lead extends through a fissure like opening or hole at an edge of the craniotomy onto a surface of the patient's brain, while a proximal portion extends proximally from the hole onto a surface of the bone table to connect to the neurostimulator. The neurostimulator has a strain relief system in the location where the proximal ends of the leads connect, to discourage the leads from unintentional disconnection.

With reference to FIGS. 1B and 1C, the neurostimulator includes a component, also referred to herein as a can, box or housing, that is placed in the ferrule that is situated in the craniectomy hole formed in the cranium. The can includes electronic components, such as a battery and a pulse generator. The neurostimulator also includes a cover assembly and a strain relief system. The cover assembly connects the leads to the electronic components in the can. The strain relief system includes a removable upper strain relief and a lower strain relief that is permanently secured to the can. The strain relief system extends from the edge of the can by a distance of 12 mm and protects the leads as they exit the can and transition onto the bone table.

After initial implant of a medical device, it may be necessary to replace the can. For example, a can replacement may be required when the battery inside the can is near its end-of-life. The procedure of replacing a can is referred to herein as a can change or box change.

During a can change, a surgical field is created by forming an opening near the end of the implanted medical device to expose the cover assembly, the strain relief system and the portions of the leads extending from the strain relief system. The surgical field encompasses the area around the implanted medical device to which access is needed in order to remove the can from the ferrule. Once the opening is formed, the upper strain relief is removed and the cover assembly is decoupled from the can. The cover assembly is removed, together with the attached leads, to the side to provide access to the can. The can is then removed from the ferrule.

After implant of the medical device, fibrotic tissue typically forms in the area around the device. While the strain relief system keeps fibrotic tissue from forming around the portions of the leads contained within the strain relief system, fibrotic tissue tends to form where the leads extends from the strain relief system and sometimes in the space between the bottom of the lower strain relief and the bone table. Such fibrotic tissue may require dissection during a can change. Dissection of tissue near the leads may result in lead damage. For example, a lead body may be cut during tissue dissection. Fibrotic tissue beneath the lower strain relief also requires dissection in order to allow for removal of the can from the ferrule.

SUMMARY

Disclosed herein are various embodiments of implantable medical devices that are configured for implant in a hole in cranium of a patient, relative to a bone table corresponding to a surface of the cranium adjacent the hole. The implantable medical devices include a can having an electrical-contact pad. The can is characterized by a form factor having a perimeter edge defining a boundary of the can, and a recessed portion with an upper surface positioned to lie beneath the bone table when the can is placed in the hole. The recessed portion supports the electrical-contact pad. The implantable medical devices also include a cover assembly having a plurality of ports. Each of the plurality of ports is configured to receive a connector end of a lead. The cover assembly is also configured to mechanically and electrically couple to the can and decouple from the can at the electrical-contact pad.

The implantable medical devices further include a strain relief system that includes a lower strain relief and an upper strain relief. The lower strain relief defines a plurality of channels, each of which is configured to receive a portion of a lead body and includes a curved portion that extends upward from a proximal end at or near the upper surface of the recessed portion to a distal end at the bone table. Each channel also includes a generally linear portion that extends from the distal end of the curved portion to a terminating end beyond the perimeter edge of the can. The upper strain relief is configured to mechanically couple to and mechanically decouple from one or both of the cover assembly and the lower strain relief, and to cover the plurality of channels of the lower strain relief when it is coupled thereto.

In a first embodiment of the implantable medical device, the lower strain relief is fixedly secured at the upper surface of the recessed portion and extends beyond the perimeter edge of the can a distance less than the upper strain relief.

In a second embodiment of the implantable medical device, the lower strain relief extends from the cover assembly. In one configuration, the lower strain relief is integral with the cover assembly. In another configuration, the lower strain relief is securely coupled to the cover assembly by features that enable the lower strain relief to be decoupled from the cover assembly. In one configuration, the lower strain relief extends beyond the perimeter edge of the can a distance about the same as the upper strain relief. In another configuration, the lower strain relief extends beyond the perimeter edge of the can a distance less than the upper strain relief and the upper strain relief includes a plurality of overbite features that extend inward in front of the terminal end of the lower strain relief.

In a third embodiment of the implantable medical device, the lower strain relief is configured to couple to the cover assembly and decouple from the cover assembly.

In a fourth embodiment of the implantable medical device, the lower strain relief is configured to couple to the upper surface of the recessed portion and decouple from the upper surface of the recessed portion.

In a fifth embodiment and a sixth embodiment of the implantable medical device, the lower strain relief includes two parts, a proximal part and a distal part. The proximal part is associated with the upper surface of the recessed portion of the can and defines the curved portion of the lower strain relief. The distal part defines the generally linear portion of the lower strain relief. In the fifth embodiment, the proximal part of the lower strain relief is configured to couple to the cover assembly and decouple from the cover assembly, and the distal part is configured to be secured to the bone table. In the sixth embodiment, the proximal part and the distal part of the lower strain relief are hinged together so that the proximal part may disassociate from the upper surface of the recessed portion of the can through rotation about the hinge.

In a seventh embodiment of the implantable medical device, the upper stain relief comprises a sheath configured to mechanically couple to a plurality of leads. The sheath includes a curved portion that extends upward from a proximal end to a distal end, and a generally linear portion that extends from the distal end of the curved portion.

BRIEF DESCRIPTION OF THE DRAWINGS

Various aspects of strain relief systems for implanted medical devices will now be presented in the detailed description by way of example, and not by way of limitation, with reference to the accompanying drawings, wherein:

FIGS. 6D and 6E are illustrations of the upper strain relief of FIG. 6A from different perspectives.

FIG. 7A is an illustration of a neurostimulator placed in a patient's cranium and having a strain relief system that includes a lower strain relief that is split into a distal part and a proximal part, and an upper strain relief.

FIG. 7B is an illustration of the neurostimulator of FIG. 7A, disassembled to show distal and proximal parts that are independent of each other.

FIG. 8A is an illustration of a neurostimulator placed in a patient's cranium and having a strain relief system that includes a lower strain relief that is split into a distal part and a proximal part that are hinged together, and an upper strain relief and.

FIG. 8B is an illustration of the neurostimulator of FIG. 8A, disassembled to show distal and proximal part that are coupled together.

DETAILED DESCRIPTION

Figure 1A:
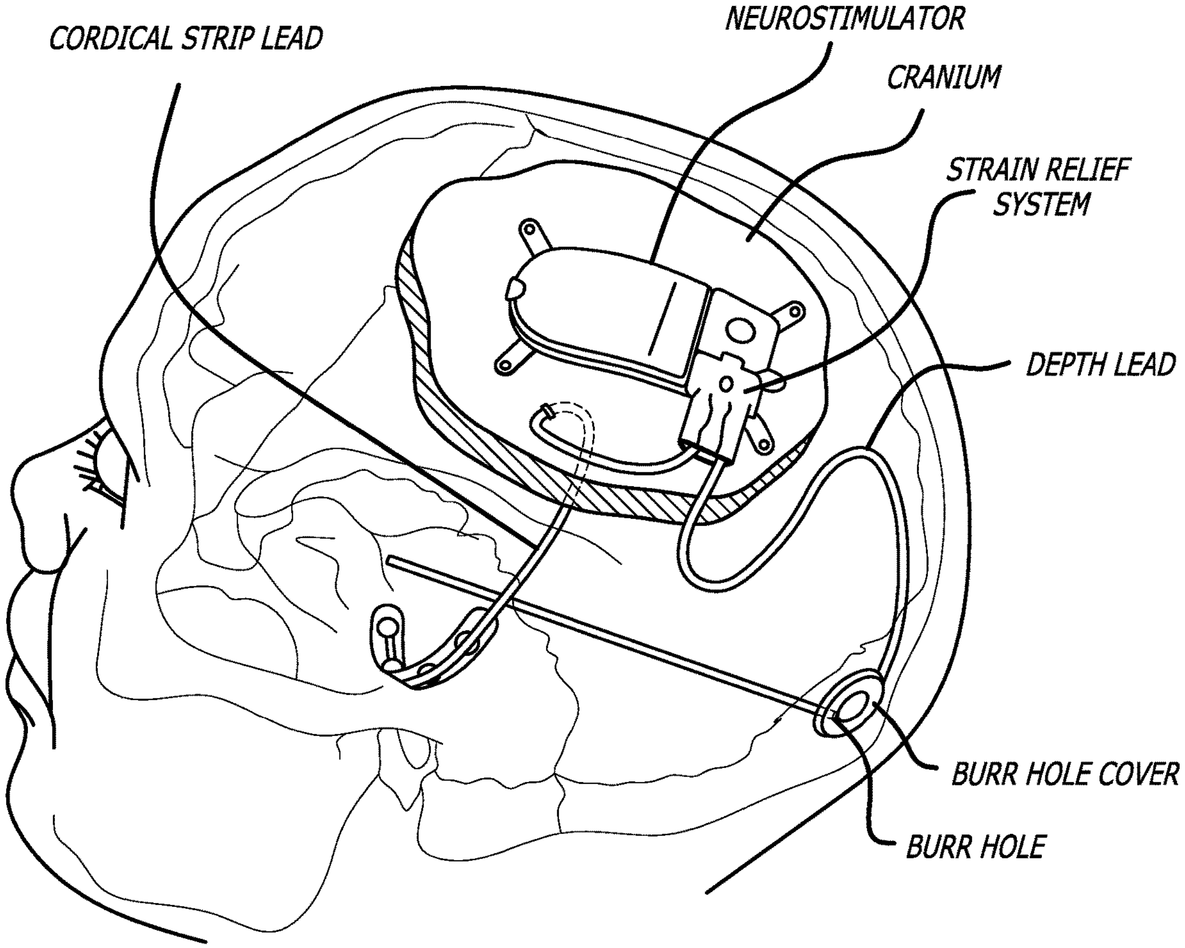
FIG. 1A is a schematic of a patient's cranium showing implanted components of a neurostimulation system, including leads and a neurostimulator.
Figure 1B:
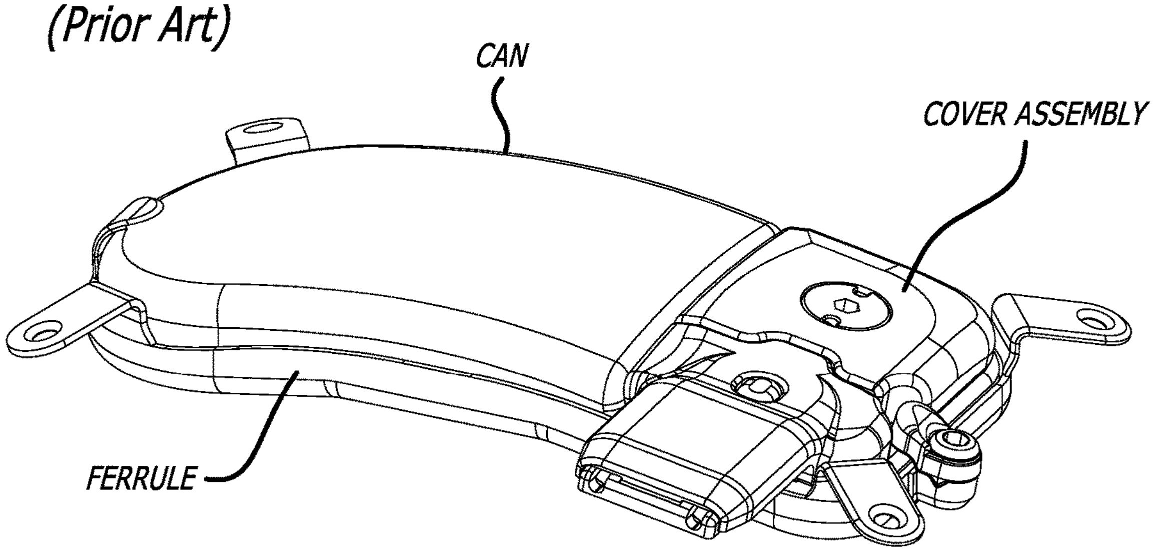
FIG. 1B (Prior Art)
FIG. 1B is an illustration of a neurostimulator placed in a ferrule and having a strain relief system that includes a lower strain relief that is integrated with a can component of the neurostimulator, and an upper strain relief.
Figure 1C:
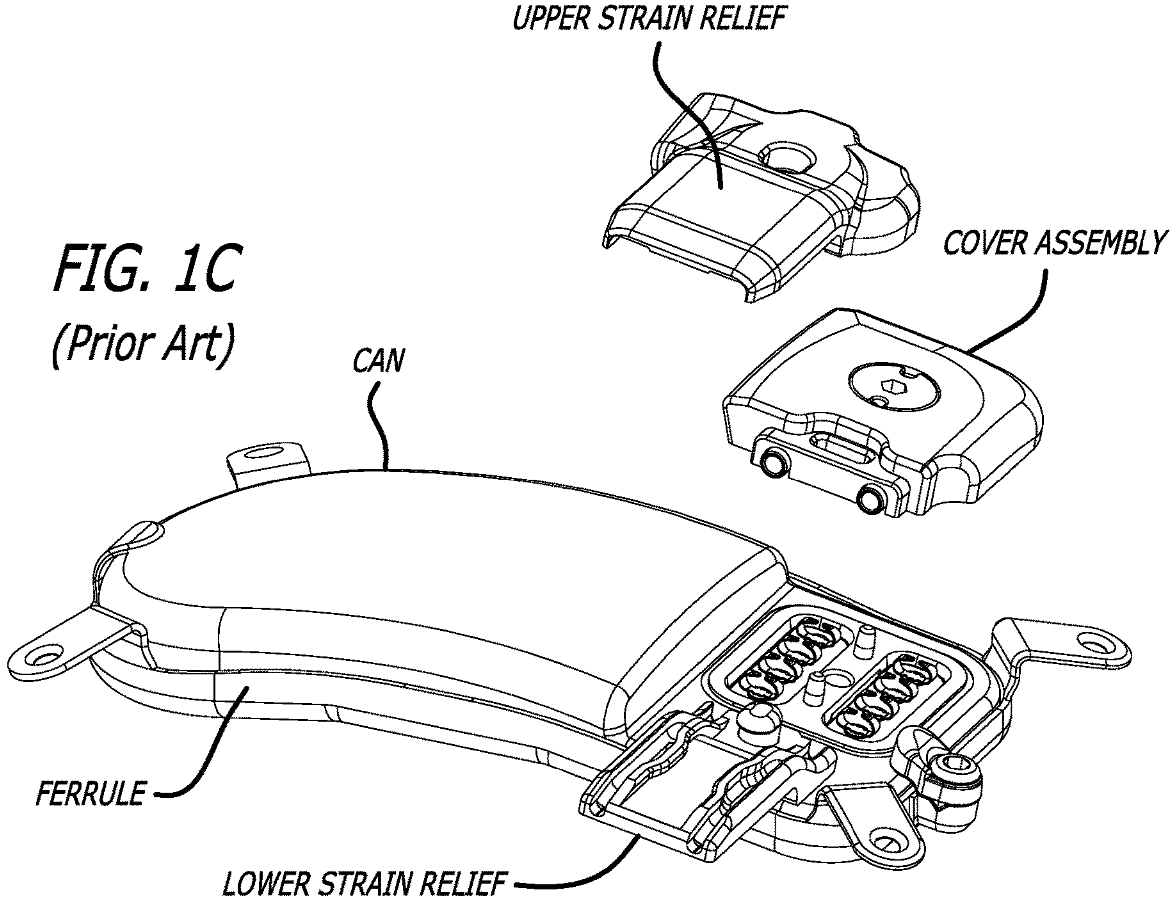
FIG. 1C (Prior Art)
FIG. 1C is an illustration of the neurostimulator of FIG. 1B, partially disassemble to show components of the neurostimulator including the lower strain relief, the upper strain relief, and a cover assembly.

Disclosed herein are various embodiments of strain relief systems for use with active implantable medical devices. The systems are configured to make can replacement procedures easier by distancing the area requiring tissue dissection from the can. To this end, some of the embodiments: 1) reduce the length of the lower strain relief and provide a longer upper strain relief that minimizes fibrotic tissue growth, 2) separate the lower strain relief from the can by incorporating the lower strain relief with the cover assembly, making the lower strain relief a stand-alone part, or removably coupling the lower strain relief to the can, and/or 3) split the lower strain relief to include a part that is secured to the can and a part that is placed on the bone table.

Throughout this disclosure the terms "proximal" and "distal" are used to describe the positions or locations of components or features of implantable medical devices, including in particular neurostimulators having a can that connects to electrode-bearing leads that extend away from the can to implant locations in or on the brain. In this context, the neurostimulator is may be described as being proximal to the leads. Or the leads may be described as extending in the distal direction from the can. The leads themselves may be described as having a proximal end that is connected to the can and a distal end that is implanted in or on the brain. Likewise, component parts of a neurostimulator may be described as having distal portions or ends and proximal portions or ends, where the distal portions or ends of these components are closer to the distal end of the lead than the proximal portions or ends.

Strain Relief System having Shortened Lower Strain Relief Integrated with Can With reference to FIGS. 2A-2H, in a first embodiment, a neurostimulator 100 includes a strain relief system having a lower strain relief 104 and an upper strain relief 102 of different lengths. The strain relief system functions to secure the leads 124 in place relative to a bone table 112 and to provide a smooth transition from the bone table 112 to a cover assembly 106, where the connector ends of the leads mechanically and electrically couple with the can 114 of the neurostimulator 100. When the neurostimulator 100 is fully assembled, each of the lower strain relief 104 and an upper strain relief 102 extends from the edge of the can 114 of the neurostimulator, with the relative extensions of each being such that the distal end 118 of the upper strain relief extends beyond the distal end 110 of the lower strain relief. The can 114 may also be referred to herein as a housing of the neurostimulator or a box of the neurostimulator.

Figure 2A:
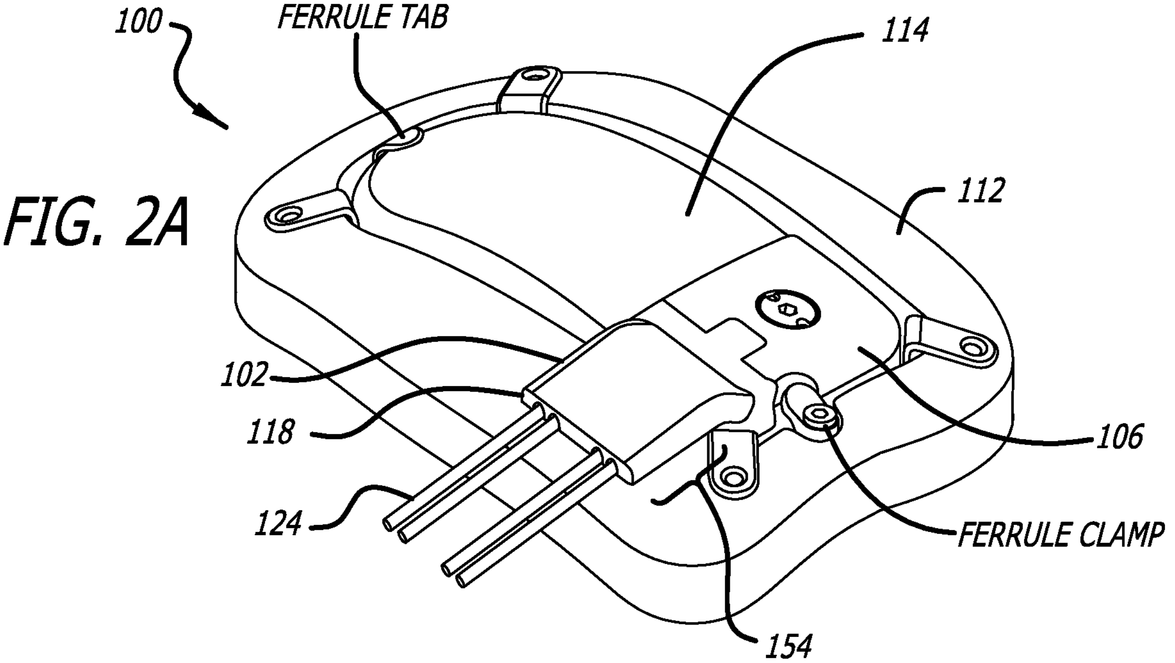
FIG. 2A is an illustration of a neurostimulator placed in a patient's cranium and having a strain relief system that includes a lower strain relief that is integrated with a can component of the neurostimulator, and an upper strain relief that extends beyond the lower strain relief.
Figure 2B:
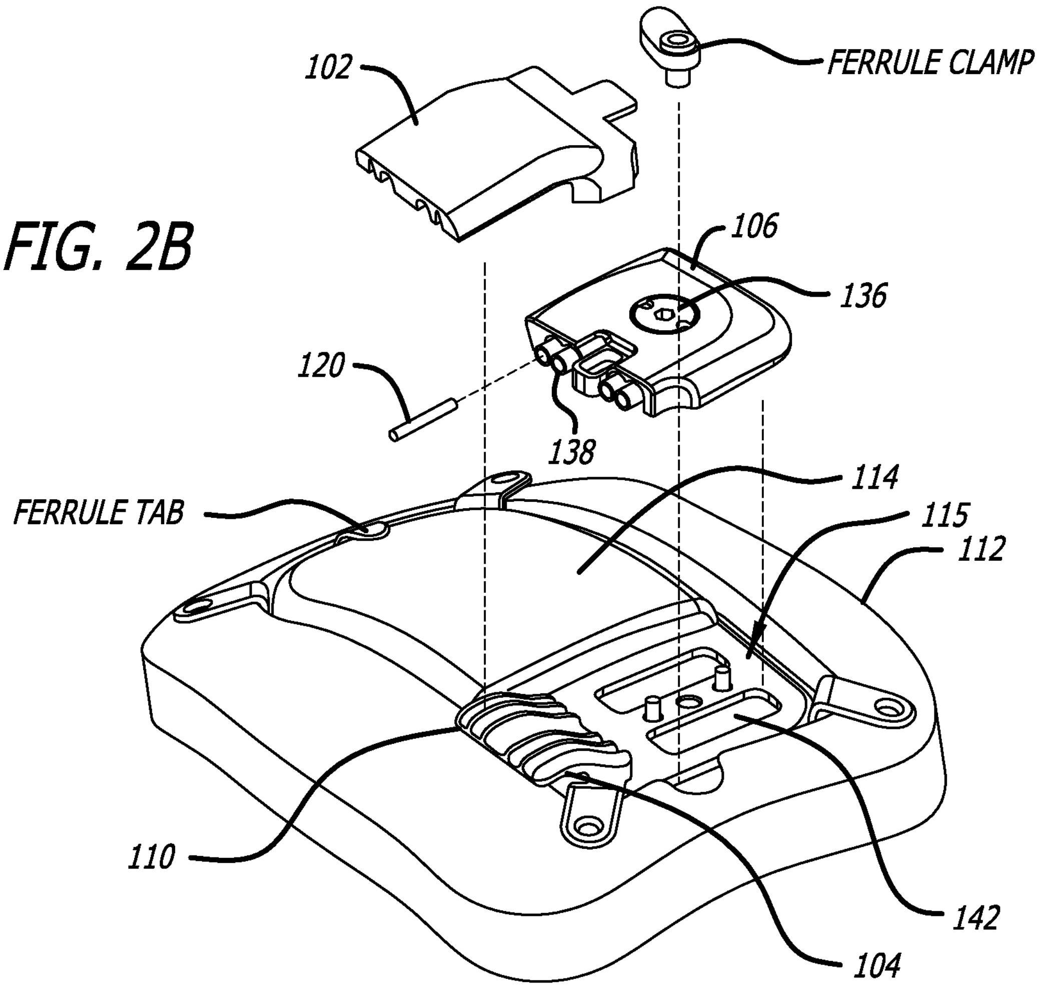
FIG. 2B is an illustration of the neurostimulator of FIG. 2A, partially disassemble to show components of the neurostimulator including the lower strain relief, the upper strain relief, and a cover assembly.
Figure 2C:
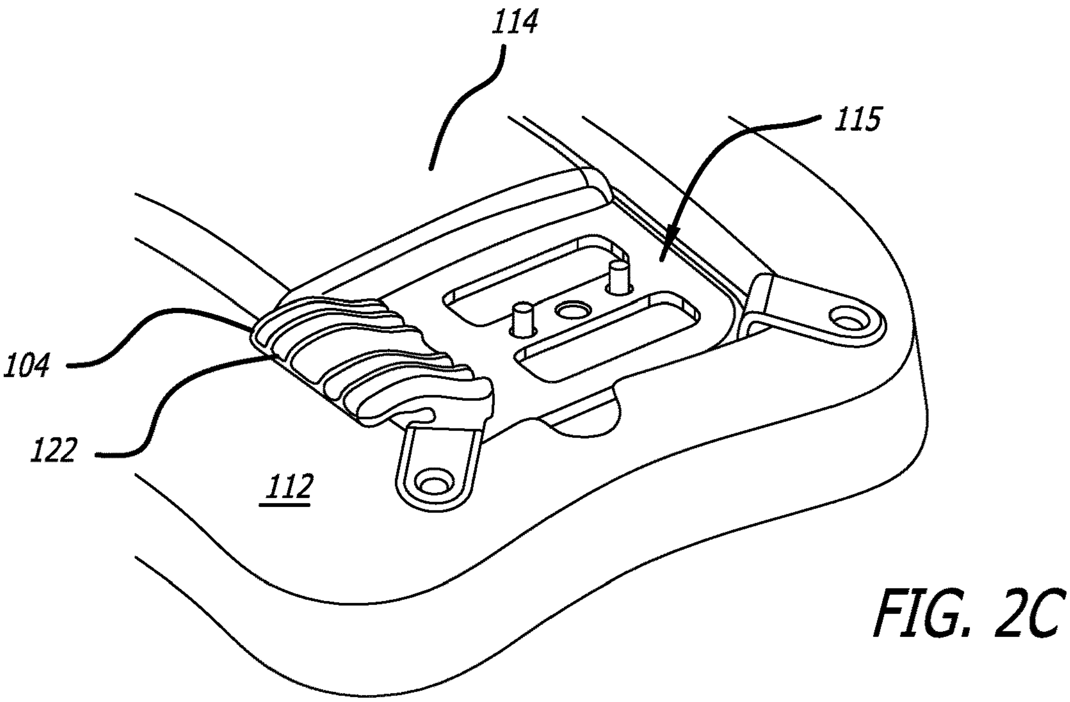
FIGS. 2C and 2D are illustrations of the neurostimulator of FIG. 2A, showing the lower strain relief from different perspectives.
Figure 2D:
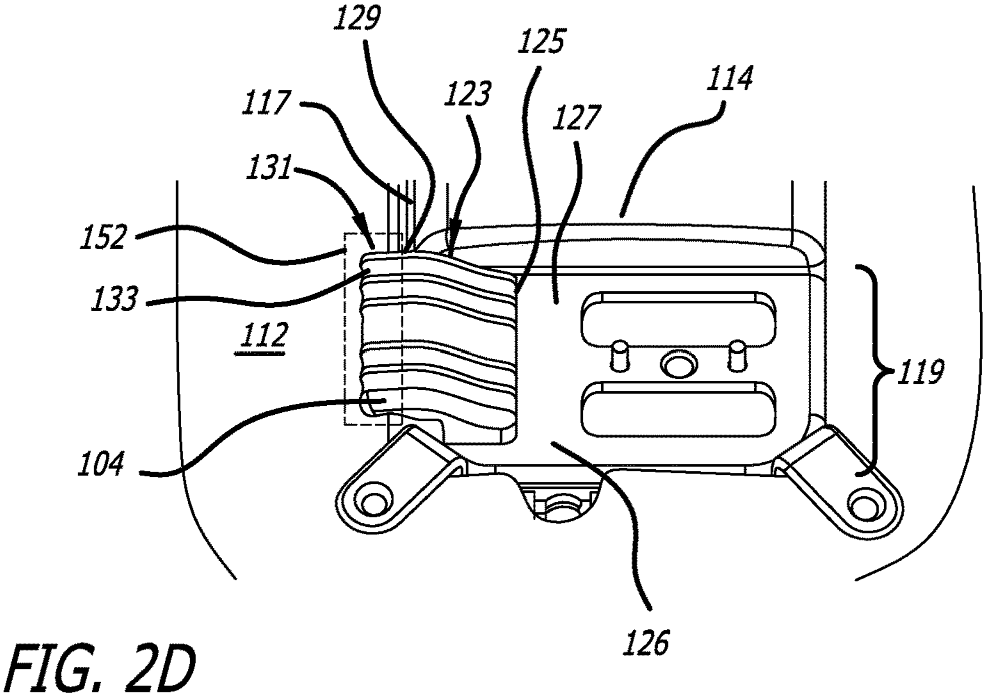

As shown in FIGS. 2A and 2D, each of the lower strain relief 104 and upper strain relief 102 includes a bone-table portion 152, 154 that extends from the edge of the can 114 over the bone table 112. The bone-table portion 152 of the lower strain relief 104 extends over the bone table 112 by a first distance, while the bone-table portion 154 of the upper strain relief 102 extends over the bone table by a second distance that is greater than the first distance. For example, the first distance may be 4 mm, while the second distance may be 12 mm.

With reference to FIGS. 2C and 2D, the lower strain relief 104 is configured and positioned relative to the can 114 such that the underside of the bone-table portion 152 of the lower strain relief sets down on the bone table 112. The lower strain relief 104 includes four channels 122 for receiving a portion of a lead body to align the leads in place. The widths of these channels 122 generally correspond to the diameter of the lead body to thereby allow for easy placement of the leads in, and removal of the leads from, the lower strain relief 104. The channels 122 are free of any reduced width sections or overhanging features that would retain the lead in place and potentially interfere with easy removal of the leads from the lower strain relief 104, for example during a can 114 replacement procedure. The lower strain relief 104 is integrated with the can 114 of the neurostimulator. The lower strain relief 104 may be made of silicone and fixed to the top of the can 114. For example, the lower strain relief may be adhered to a lower surface 126 of the can 114.

Figure 2E:
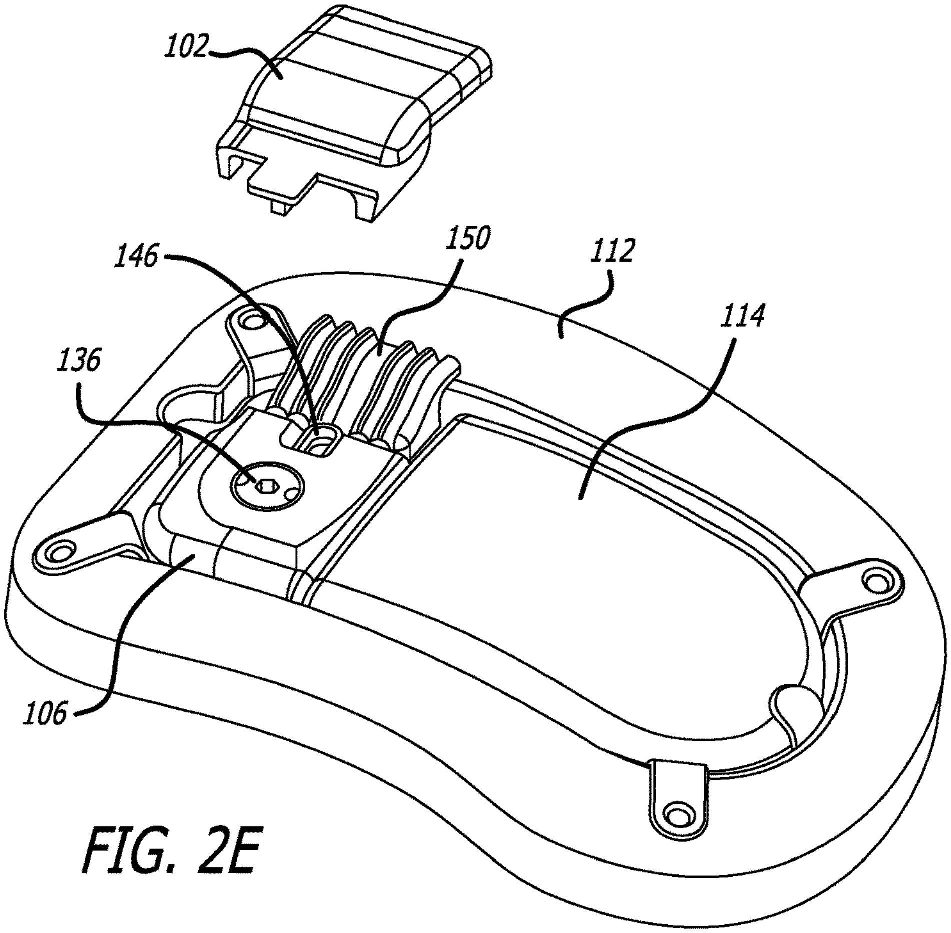
FIG. 2E is an illustration of the neurostimulator of FIG. 2A from a different perspective, partially disassemble to show the upper strain relief separated from the other components of the neurostimulator.
Figure 2F:
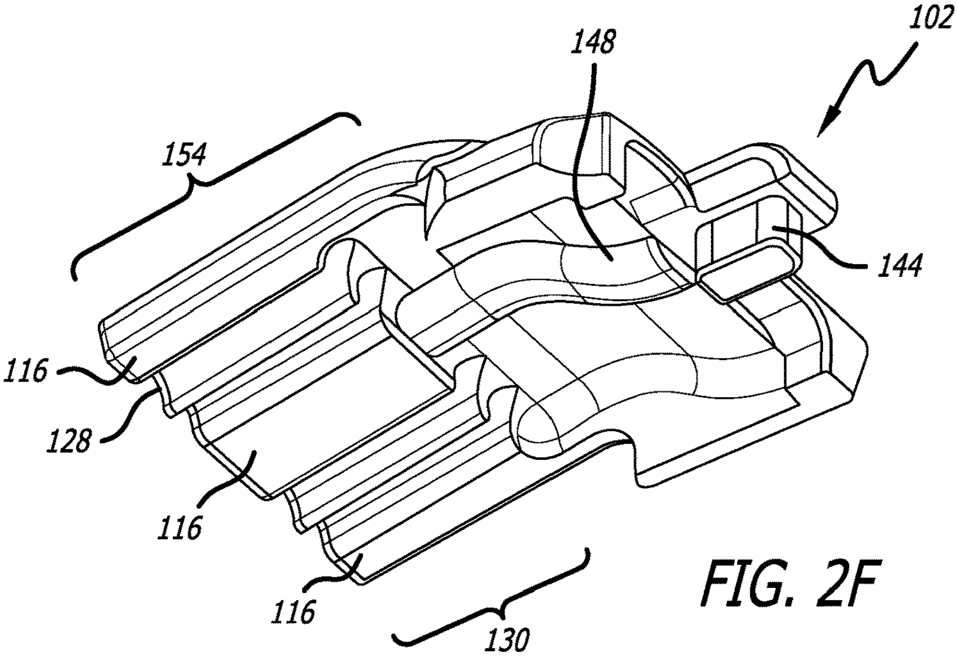
FIG. 2F is an illustration of the underside of the upper strain relief shown in FIG. 2E.

With reference to FIG. 2F, the bone-table portion 154 of the upper strain relief 102 includes a distal region 130 having four channels 128 for receiving a portion of a lead body to align the leads in place. Like the channels 122 of the lower strain relief 104, the widths of these channels 128 generally correspond to the diameter of the lead body to thereby allow for easy placement of the leads in, and removal of the leads from, the upper strain relief 102. The distal region 130 of the bone-table portion 154 includes several surface regions 116. The thickness of the distal region 130 is such that these surface regions 116 set down onto the bone table 112 when the upper strain relief 102 is coupled in place over the lower strain relief 104. The thickness may be 2.7 (3.0) mm. These surface regions 116 thus fill the space between the top of the bone-table portion 154 of the upper strain relief 102 and the bone table 112. This is beneficial as it minimizes the formation of fibrotic tissue in that space and makes can replacement easier. The upper strain relief 102 may be made of silicone material either harder and stiffer or softer and more flexible than the lower strain relief 104. The upper strain relief 102 may be reinforced with mesh material to provide additional protection of the leads from potential damage during cutting of the scalp during a can 114 replacement procedure.

Figure 2G:
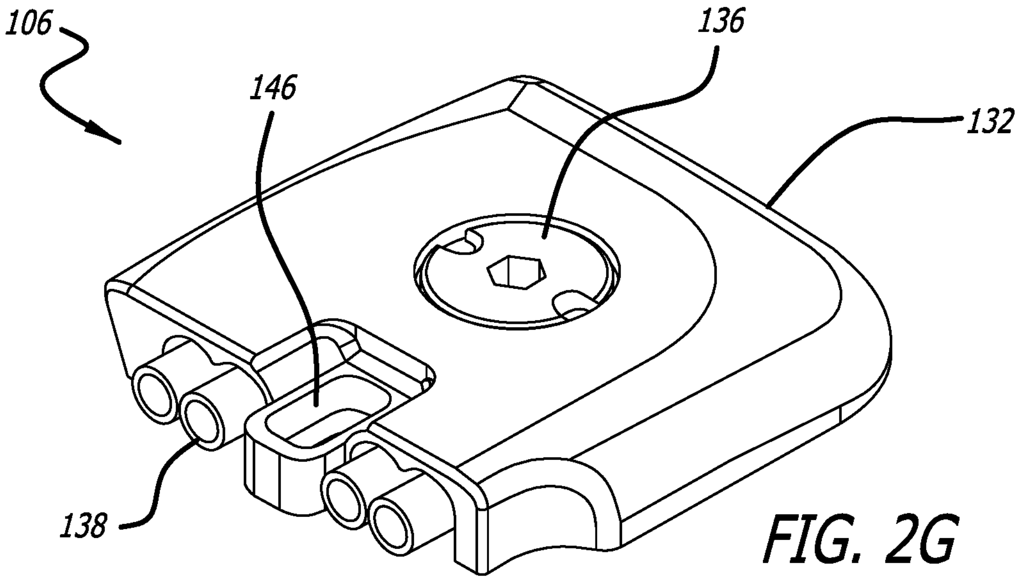
FIGS. 2G and 2H are illustrations of the cover assembly of the neurostimulator of FIG. 2A, from different perspectives.
Figure 2H:
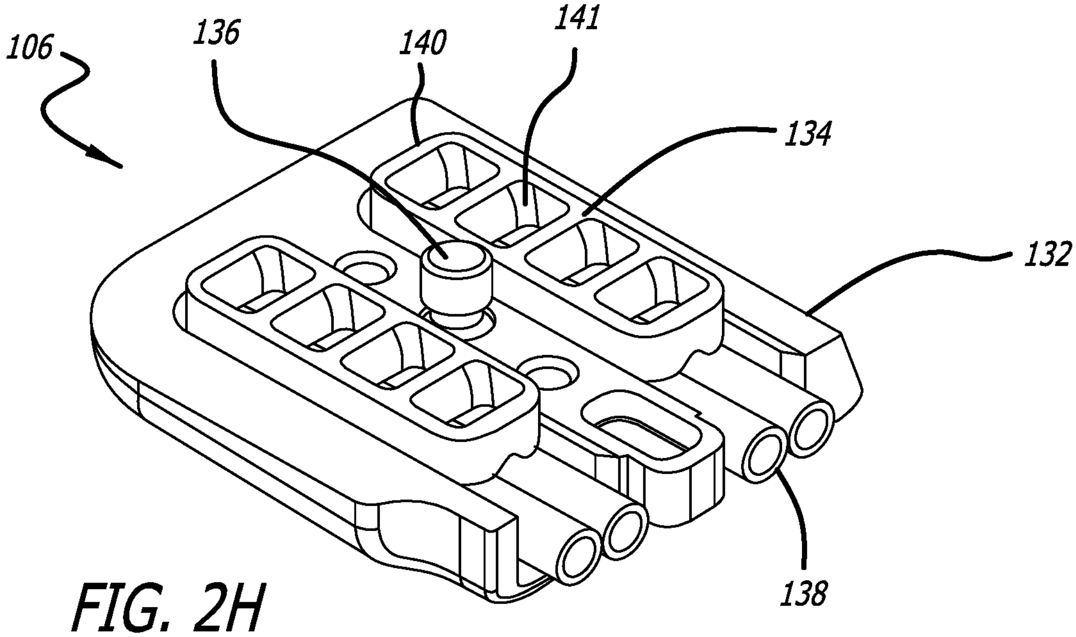

With reference to FIGS. 2G and 2H the cover assembly 106 includes a housing 132, a pair of seals 134, and a coupling mechanism 136. Each seal 134 includes a pair of tubular inserts 138, each configured to receive a connector end of a lead, and a footing 140 having a plurality of opening 141. Thus, the cover assembly 106 is configured to accommodate four leads. The coupling mechanism 136 is configured to secure the cover assembly 106 to the can 114. To this end, and with additional reference to FIG. 2, the region of the can 114 that receives the cover assembly 106 includes alignment features, e.g., a pair of posts, and a locking feature, e.g., a hole, that mate with corresponding alignment and locking features of the cover assembly, which features are shown in FIG. 2H. When the cover assembly 106 is aligned with the can and secured to the can 114 by the coupling mechanism 136, the footings 140 mate with contact recesses 142 and electrical connection is established between contacts on the lead connectors that are inserted in the tubular inserts 138 and contacts (not shown in FIG. 2B) on the neurostimulator can.

Having described the structure of a first embodiment of a neurostimulator 100 having a strain relief system, procedures related to initial neurostimulator implant and neurostimulator can replacement are now described.

With reference to FIG. 2A-2H, during initial implant of the first embodiment of a neurostimulator 100, the neurostimulator can 114 is secured within a ferrule implanted in a patient's cranium 108 using known techniques. For example, a ferrule tab may be bent over the top of the can 114 to secure it in place. The distal, electrode-bearing ends of one or more leads 124 are implanted in the brain using known techniques. Proximal portions of the one or more leads extend from a hole in the skull and are secured in place at the surface or bone table 112 of the skull using, for example, a burr hole cover. The connector end 120 of each of the one or more leads 124 is inserted into a corresponding tubular insert 138 of the cover assembly 106 and fully seated. Marker bands on the leads 124 are used to indicate when a lead is fully seated.

With reference to FIGS. 2B and 2E, the cover assembly 106 is mechanically and electrically coupled to the can 114. To this end, the footings 140 of the cover assembly 106 are mated with the contact recesses 142 of the can 114 and the cover assembly is partially secured to the can 114 using the coupling mechanism 136. A ferrule clamp may also be used to further secure the cover assembly.

With reference to FIG. 2E, a portion of each lead (not shown for clarity) that is connected to the cover assembly 106 is placed in a corresponding channel 122 of the lower strain relief 104. Next, the cover assembly 106 is fully secured to the can 114 using the coupling mechanism 136.

With reference to FIGS. 2E and 2F, the upper strain relief 102 is then placed over the lower strain relief 104 to align each respective channel 128 of the upper strain relief with a portion of a lead body extending from the end of the lower strain relief. The upper strain relief 102 is then coupled to the top of the lower strain relief 104 and to the cover assembly 106 by various mating features. These mating features include, for example, a tab 144 of the upper strain relief 102 and a hole 146 of the cover assembly 106, and a ramped protrusion 148 of the upper strain relief 102 and a ramped channel 150 of the lower strain relief.

With reference to FIGS. 2A-2H, during a can 114 replacement procedure, a surgical opening is created through the scalp, near the cover assembly 106 end of the neurostimulator 100. The opening is large enough to expose the cover assembly 106, the upper strain relief 102 and the portions of the leads 124 extending from the strain relief system.

With reference to FIG. 2A, the upper strain relief 102 is removed to expose the lower strain relief 104. The cover assembly 106 is decoupled from the can 114 by loosening the coupling mechanism 136. The cover assembly is then pulled away from the can in the direction of the lower strain relief 104. In doing so, the portions of the leads 124 resting in place in the channels 122 of the lower strain relief 104 are removed from the channels and the cover assembly 106 (with leads still connected) is able to be displaced from the surgical field surrounding the can 114.

Any fibrotic tissue in the area of the lower strain relief 104 is dissected with the leads 124 far removed from the area of dissection to eliminate potential lead damage. The can 114 with the lower strain relief 104 relief attached is then removed from the ferrule by removing a ferrule clamp and sliding the can out from under the bent ferrule tab by lifting the recessed end of the can up slightly and pulling the can out in the direction of where the ferrule clamp was located. A new can 114 is placed and secured in the ferrule using the ferrule clamp and ferrule tab. Then appropriate steps of the initial implant procedure described above are performed to complete the can replacement procedure.

Thus disclosed is a first embodiment of implantable medical device 100 configured for implant in a hole in cranium of a patient, relative to a bone table 112 corresponding to a surface of the cranium adjacent the hole. The implantable medical device 100 includes a can 114 having an electrical-contact pad 115. The can 114 is characterized by a form factor having a perimeter edge 117 defining a boundary of the can, and a recessed portion 119 with an upper surface 127 positioned to lie beneath the bone table 112 while the can is placed in the hole, and that supports the electrical-contact pad 115. The implantable medical device 100 also includes a cover assembly 106 having a plurality of ports 138, each configured to receive a connector end 120 of a lead 124. The cover assembly 106 is configured to couple to the can 114 and decouple from the can at the electrical-contact pad 115. The implantable medical device also includes a strain relief system that includes a lower strain relief 104 and an upper strain relief 102. The lower strain relief defines a plurality of channels 122, each configured to receive a portion of a lead 124 body, and includes a curved portion 123 and a generally linear portion 131. The curved portion 123 extends upward from a proximal end 125 at or near the upper surface 127 of the recessed portion 119 to a distal end 129 at the bone table 112. The generally linear portion 131 extends from the distal end 129 of the curved portion to a terminating end 133 beyond the perimeter edge 117 of the can 114. The upper strain relief 102 is configured to mechanically couple to and mechanically decouple from one or both of the cover assembly 106 and the lower strain relief 104. The upper strain relief 102 covers the plurality of channels 122 of the lower strain relief 104. The lower strain relief 104 is fixedly secured at the upper surface 127 of the recessed portion 119 and extends beyond the perimeter edge 117 of the can 114 a distance less than the upper strain relief 102.

In the first embodiment of a neurostimulator 100, the shorter design of the lower strain relief 104 in combination with the upper strain relief 102 setting on the bone table 112 makes the can 114 replacement procedure less cumbersome. The upper strain relief 102 minimizes the growth of fibrotic tissue between it and the bone table 112, thereby the presence of fibrotic tissue is limited to the area of the lower strain relief 104. The lower strain relief 104, however, extends from the can onto the bone table 112 a short distance. Thus, the amount of fibrotic tissue requiring dissection in order to remove the can 114 from the ferrule is minimal and the procedure for replacing the can is made easier.

Strain Relief System with Integrated Lower Strain Relief and Cover Assembly

With reference to FIGS. 3A-3G and FIGS. 4A-4J, in a second embodiment, a neurostimulator 200*a*, 200*b* includes a strain relief system having an upper strain relief 202*a*, 202*b*, and a pair of lower strain reliefs 204*a*, 204*b* that are integrated with or coupled to a cover assembly 206*a*, 206*b* of the neurostimulator. A first configuration of the neurostimulator 200*a* is shown in FIGS. 3A-3G, while a second configuration of the neurostimulator 200*b* is shown in FIGS. 4A-4J. In each configuration, the strain relief system functions to secure leads in place relative to a bone table 212*a*, 212*b* and to provide a smooth transition for the lead from the surface of the bone table down to the cover assembly 206*a*, 206*b*, where the connector ends of the leads mechanically and electrically couple with the can 214*a*, 214*b* of the neurostimulator 200*a*, 200*b*. The lower strain reliefs 204*a*, 204*b* may be made of silicone. The upper strain reliefs 202*a*, 202*b* may be made of silicone material either harder and stiffer or softer and more flexible than the lower strain reliefs 204*a*, 204*b*. The upper strain relief 202*a*, 202*b* may be reinforced with mesh material to provide additional protection of the leads from potential damage during cutting of the scalp during a can 214*a*, 214*b* replacement procedure.

Figure 3A:
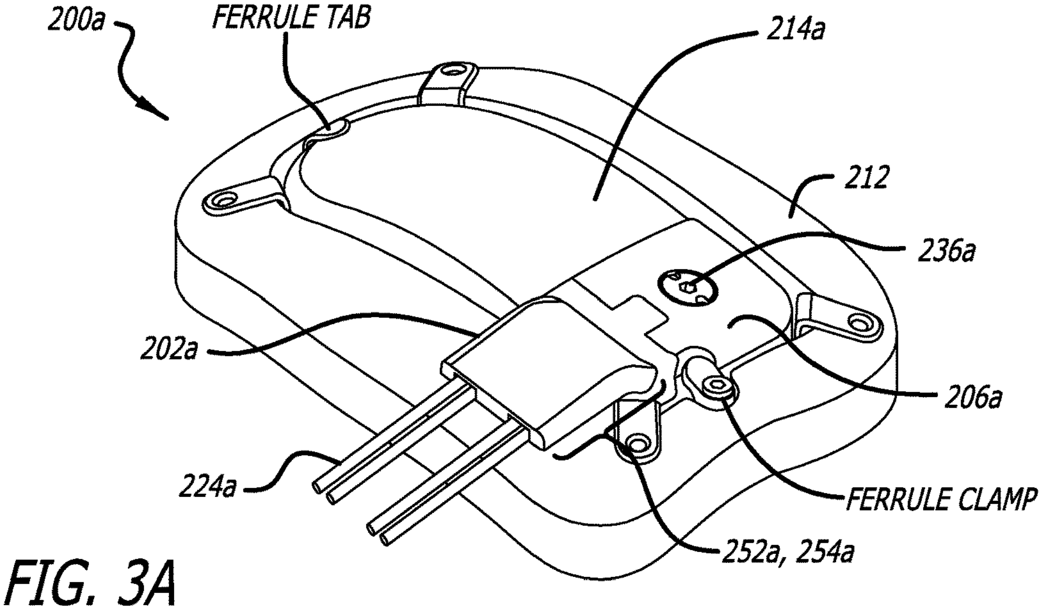
FIG. 3A is an illustration of a neurostimulator placed in a patient's cranium and having a strain relief system that includes an upper strain relief, and a pair of lower strain reliefs that are integrated with a cover assembly of the neurostimulator.
Figure 3B:
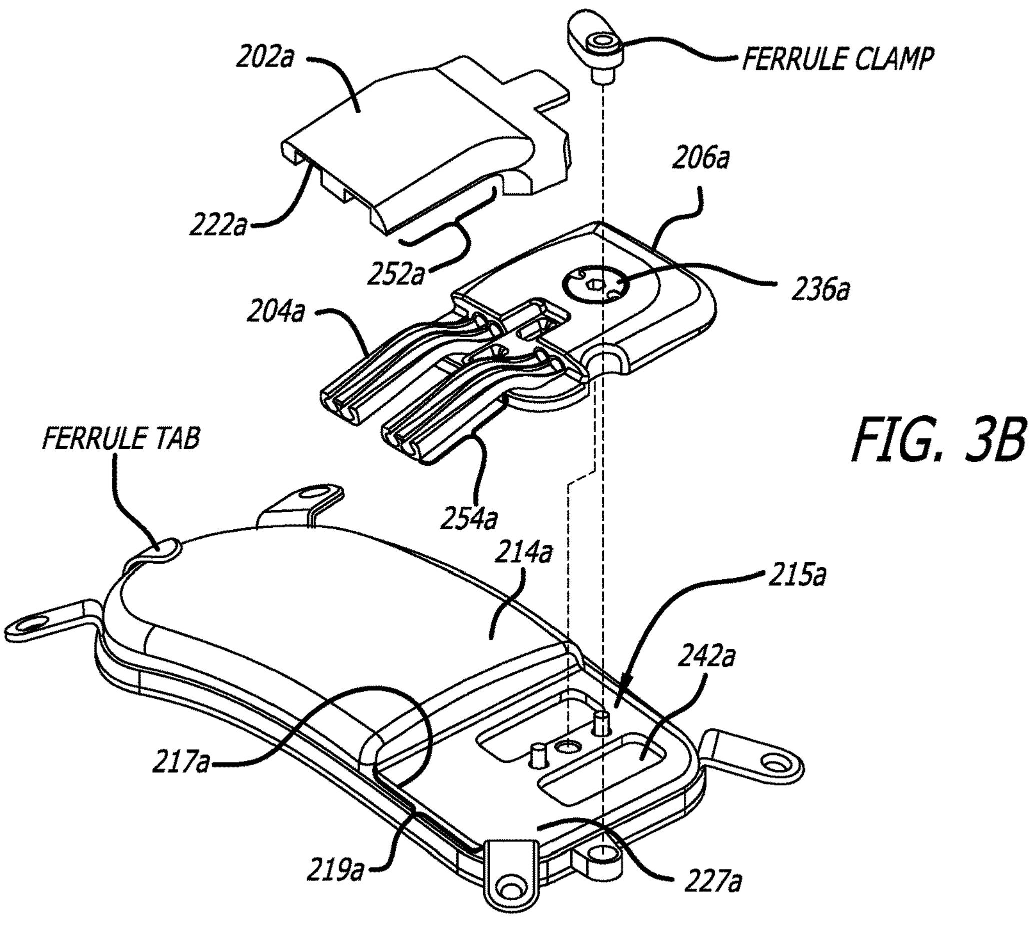
FIG. 3B is an illustration of the neurostimulator of FIG. 3A, partially disassemble to show components of the neurostimulator including the upper strain relief, and the lower strain reliefs integrated with the cover assembly.

With reference to FIGS. 3A and 3B, in the first configuration of the second embodiment of the neurostimulator 200*a* each of the lower strain reliefs 204*a* and the upper strain relief 202*a* includes a bone-table portion 252*a*, 254*a* that extends from the edge of the can 214*a* over the bone table 212. The bone-table portion 252*a* of the lower strain reliefs 204*a* extends over the bone table 212 by a first distance, while the bone-table portion 254*a* of the upper strain relief 202*a* extends over the bone table by a second distance that is generally equal to the first distance, but may be slightly greater or less than the first distance. For example, the first distance and the second distance may be 12 mm. Accordingly, as shown in FIGS. 3F and 3G, the respective distal ends of the lower strain reliefs 204*a* and the upper strain relief 202*a* terminate at the same point on the bone table 212.

Figure 3C:
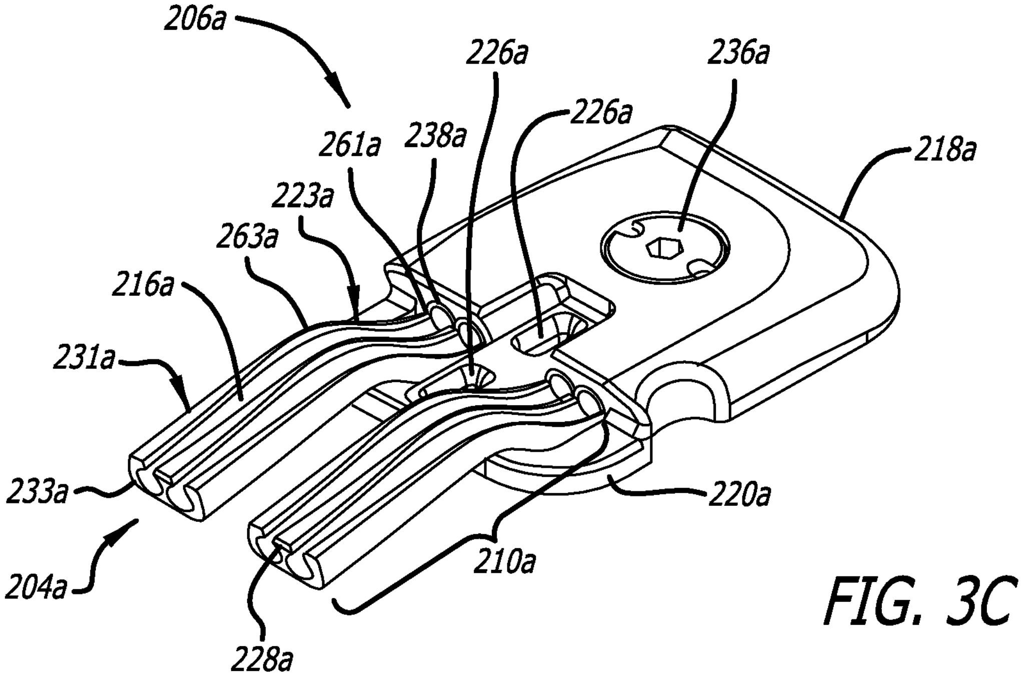
FIGS. 3C and 3D are illustrations of the integrated lower strain reliefs and cover assembly of the neurostimulator of FIG. 3A, from different perspectives.
Figure 3D:
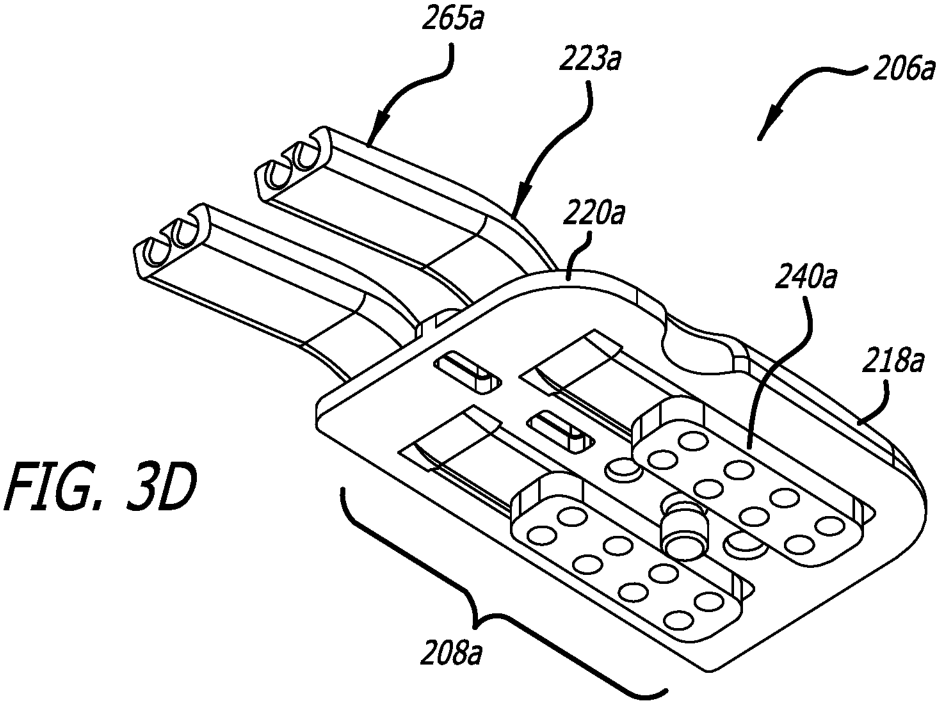

With reference to FIGS. 3A, 3C and 3D, the lower strain reliefs 204*a* include a seal portion 208*a* and a strain relief portion 210*a*. Like the seal described above with reference to FIGS. 2G and 2H, the seal portion 208*a* includes a pair of tubular inserts 238*a* (visible in FIG. 3C), each configured to receive a connector end of a lead, and a footing 240*a* (shown in FIG. 3D) having a plurality of windows. The strain relief portion 210*a* extends away from the tubular inserts 238*a* and ramps up onto the bone table 212*a*.

The strain relief portions 210*a* are open on top and includes a pair of channels 216*a*. During implant, the connector end of leads are inserted into the tubular inserts 238*a* and the lead body is placed into a channel 216*a* of the strain relief portion 210*a*. The channels 216*a* guide the connector ends of the leads into the tubular inserts and make lead connection easier. The widths of these channels 216*a* generally correspond to the diameter of the lead body to thereby allow for easy placement of the leads in, and removal of the leads from, the lower strain reliefs 204*a*. The channels 216*a*, however, do include a reduced width section or overhanging features 228*a* that retain the lead in place. The lead is thereby retained in the strain relief 204*a* to minimize movement of the lead while other leads are being inserted into the tubular inserts 238*a* and to prevent the leads from moving during subsequent assembly of the cover assembly 206*a* to the can 214*a*. The cover assembly 206*a* includes a housing 218*a* with a pair of mating features 226*a* for engaging the upper strain relief 202*a*, and a coupling mechanism 236*a* like that described above with reference to FIGS. 2G and 2H.

With continued reference to FIGS. 3C and 3D, part 220*a* of the housing 218*a* of the cover assembly 206*a* extends around and underneath the strain relief portions 210*a* to help support the strain relief portions. This part 220*a* of the housing 218*a* also helps lift the strain relief portions 210*a* up when the cover assembly 206*a* is being removed from the can 214*a* during can replacement.

With reference to FIGS. 3B, 3E, 3F and 3G, the upper strain relief 202*a* includes two channels 222*a* in its underside. Each of these channels 222*a* is sized to receive a lower strain relief portion 210*a*. The upper strain relief thus, in essence, wraps around the lower strain reliefs (except for their underneath surfaces) and fills the space between the lower strain reliefs to thereby present a substantially continuous underneath surface (as best seen in FIG. 3G) that rests onto of the bone table 212*a* and thus, minimizes the formation of fibrotic tissue around the lower strain reliefs.

The upper strain relief 202*a* includes one or more coupling features 225*a* configured to mate with corresponding coupling features 226*a* associated with the cover assembly 206*a*. When the upper strain relief 202*a* is pushed onto the cover assembly 206*a*, these coupling features 225*a*, 226*a* engage to position and retain the upper strain relief in place on the cover assembly.

Figure 3F:
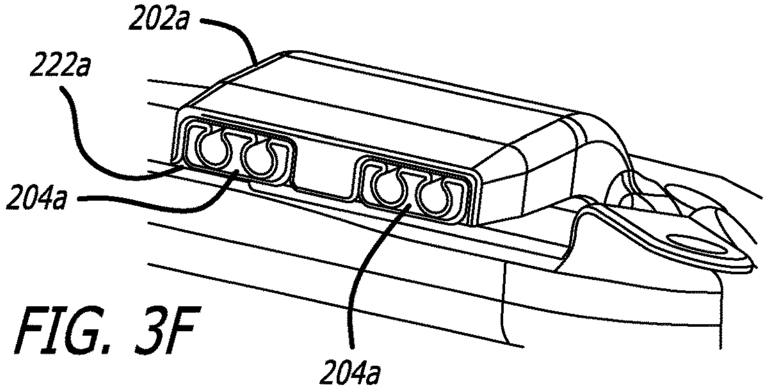
FIGS. 3F and 3G are illustrations of the neurostimulator of FIG. 3A, showing the upper strain relief and the lower strain reliefs from different perspectives.
Figure 3G:
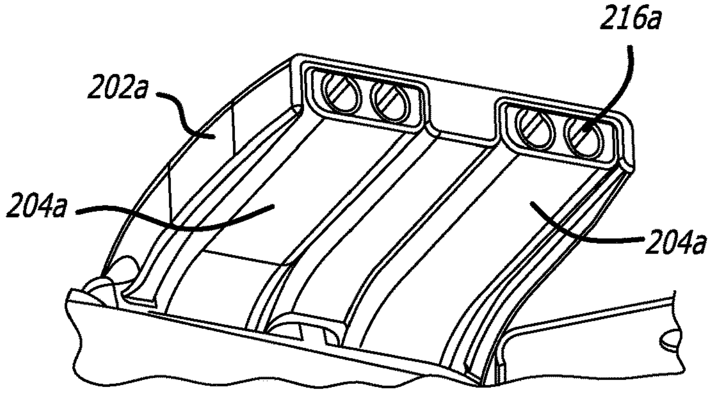
Figure 4A:
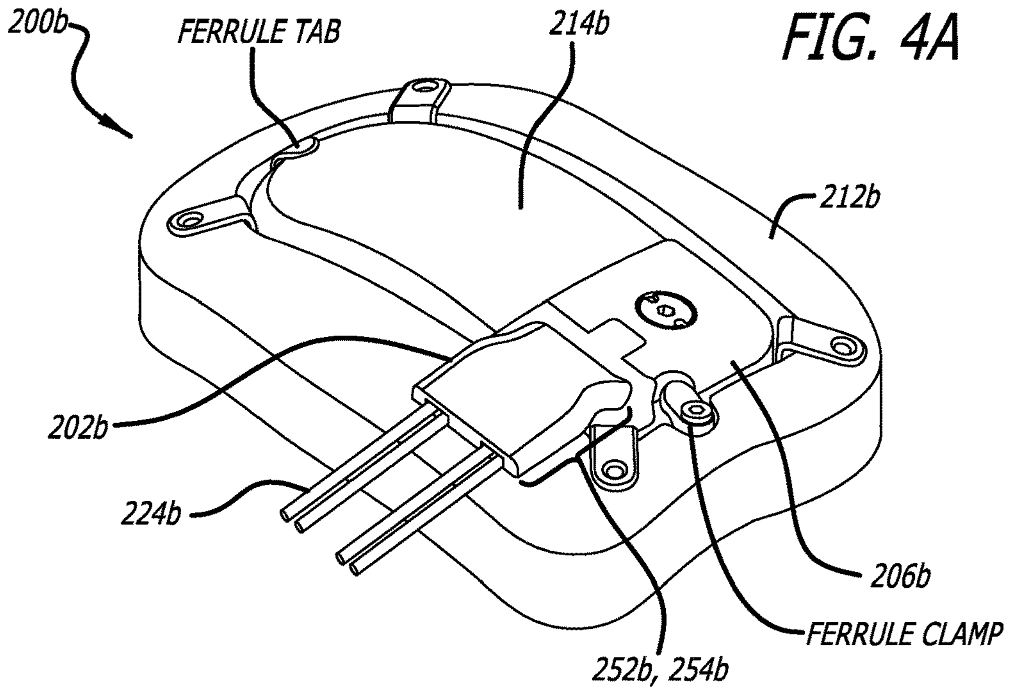
FIG. 4A is an illustration of a neurostimulator placed in a patient's cranium and having a strain relief system that includes an upper strain relief, and a pair of lower strain reliefs that are integrated with a cover assembly of the neurostimulator.
Figure 4B:
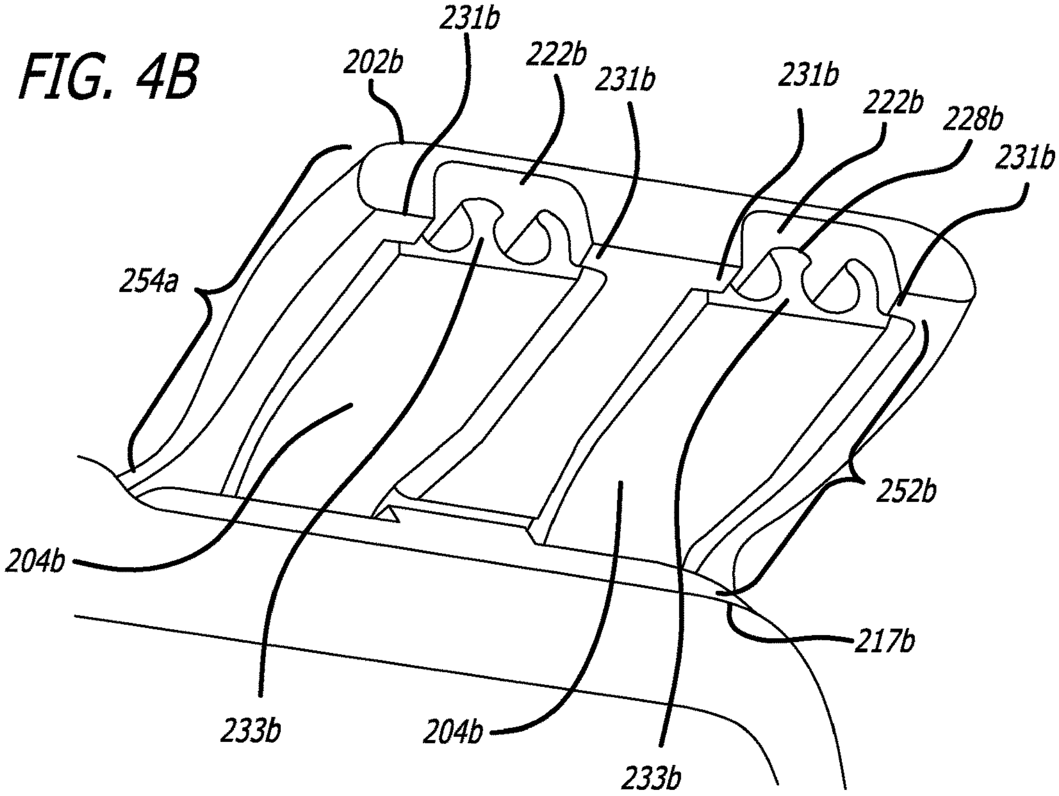
FIGS. 4B and 4C are illustrations of the neurostimulator of FIG. 4A, showing the undersides of the upper strain relief and the lower strain reliefs.
Figure 4C:
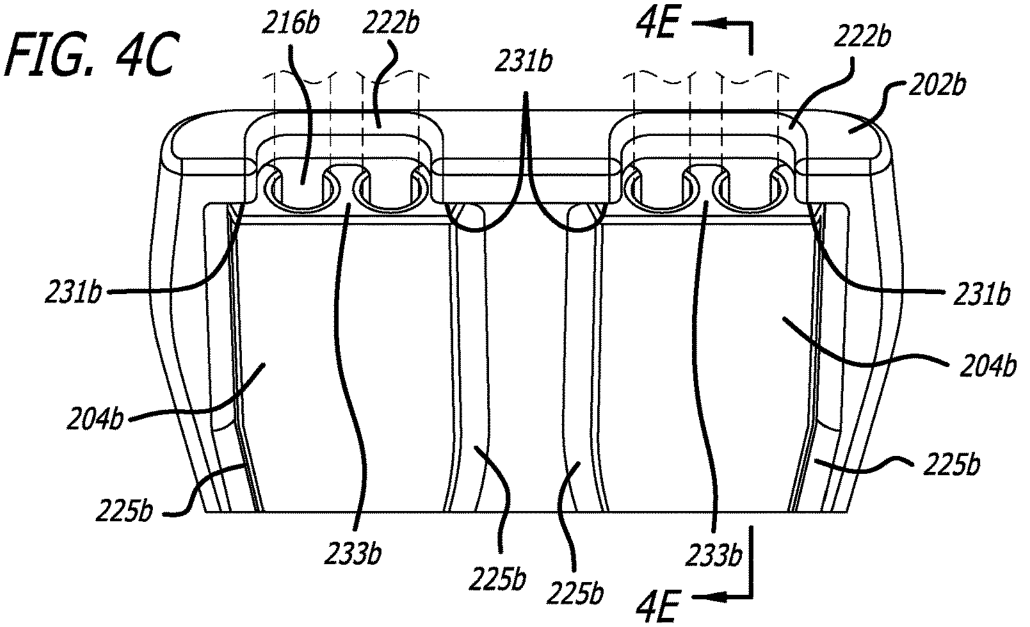

With reference to FIGS. 4A, 4B, and 4C, in the second configuration of the second embodiment of the neurostimulator 200*b* each of the lower strain reliefs 204*b* and the upper strain relief 202*b* includes a bone-table portion 252*b*, 254*b* that extends from the edge of the can 214*b* over the bone table 212. The bone-table portion 252*b* of the lower strain reliefs 204*b* extends over the bone table 212 by a first distance, while the bone-table portion 254*b* of the upper strain relief 202*a* extends over the bone table by a second distance that is generally equal to the first distance, but may be slightly greater or less than the first distance. For example, the first distance may be 12 mm, while the second distance may be 10 mm. Accordingly, as shown in FIGS. 3F and 3G, the respective distal ends of the lower strain reliefs 204*b* and the upper strain relief 202*b* terminate at different points on the bone table 212.

Figure 4D:
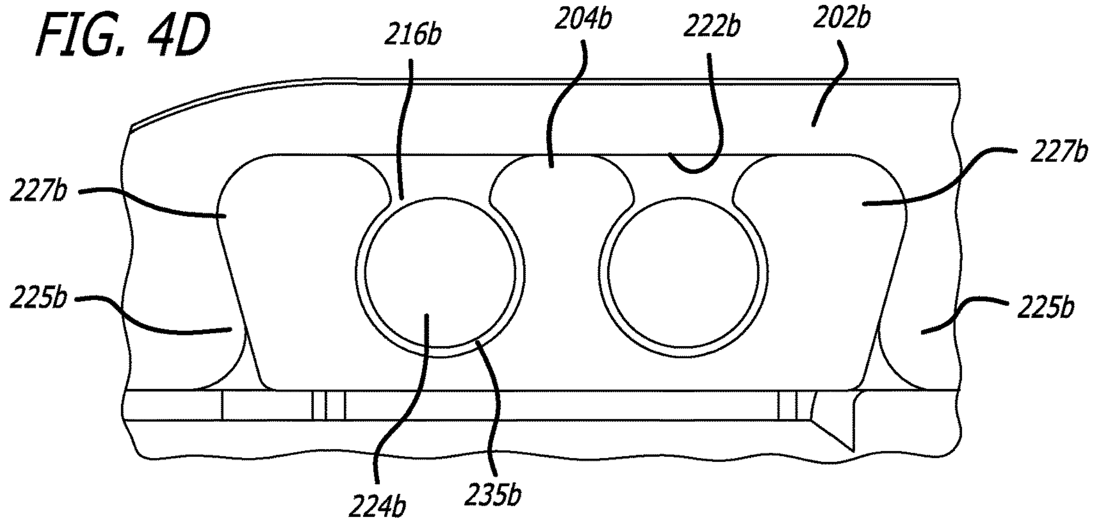
FIG. 4D is an end-view illustration of the neurostimulator of FIG. 4A, showing the upper strain relief and a lower strain relief.
Figure 4E:
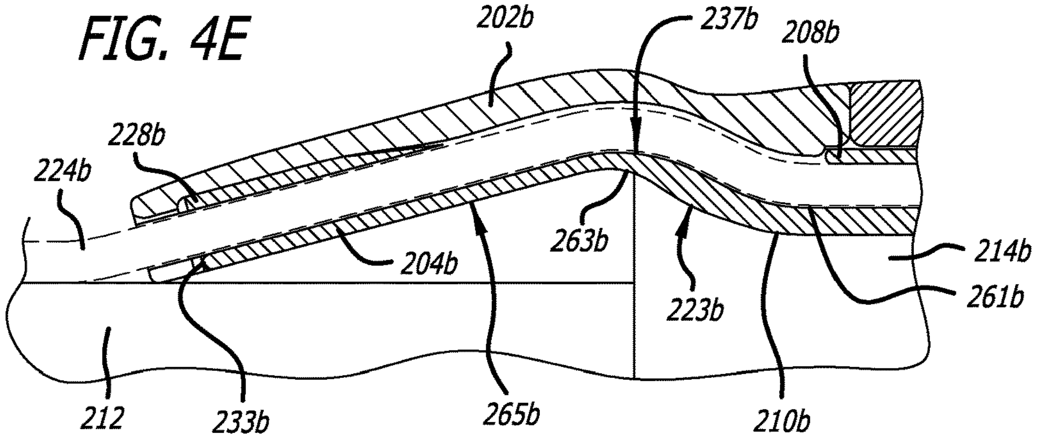
FIG. 4E is an side-view, cross-section illustration of the neurostimulator of FIG. 4A, showing an upper strain relief, a lower strain relief and portions of a cover assembly.
Figure 4F:
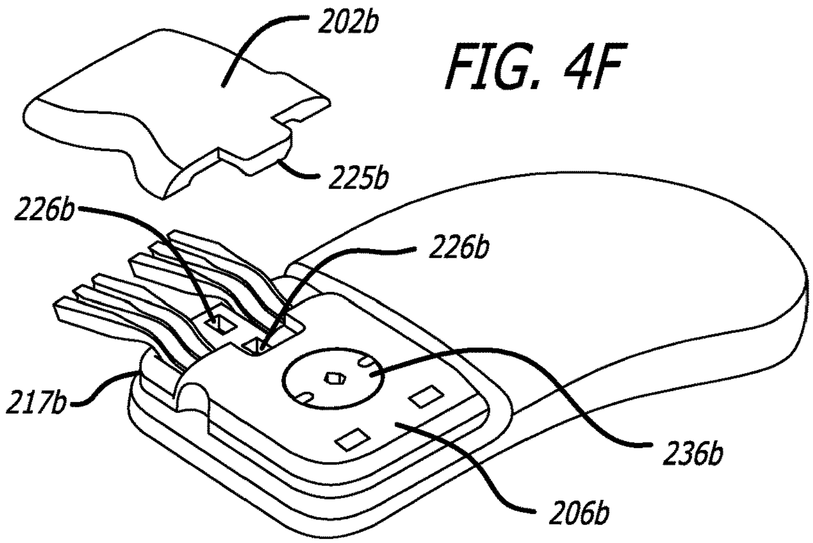
FIG. 4F is an illustration of the neurostimulator of FIG. 4A from a different perspective, partially disassemble to show the upper strain relief separated from the other components of the neurostimulator.
Figure 4G:
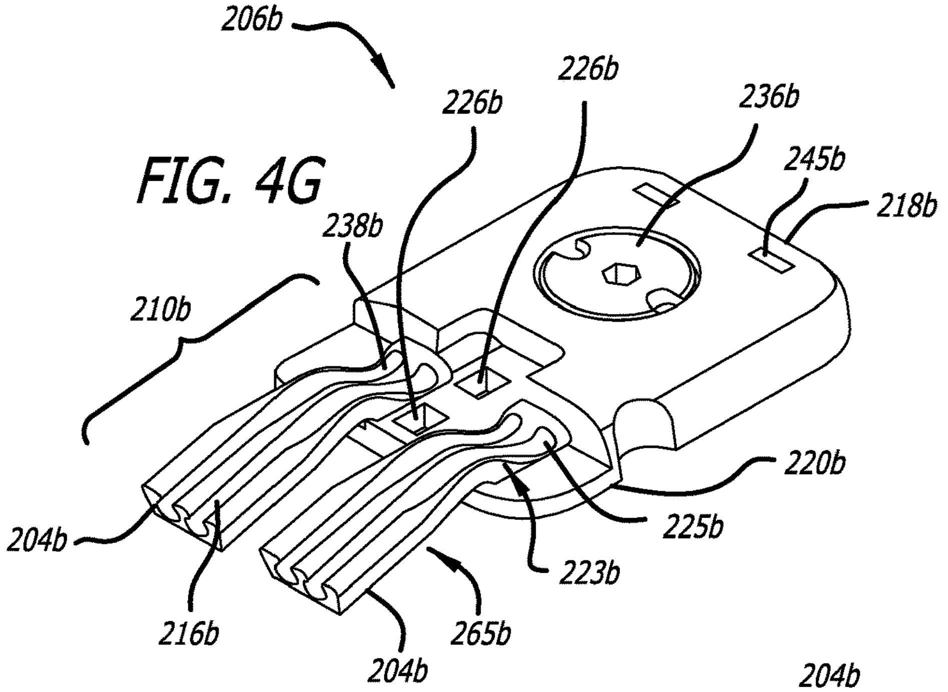
FIGS. 4G and 4H are illustrations of the integrated lower strain reliefs and cover assembly of the neurostimulator of FIG. 4A, from different perspectives.
Figure 4H:
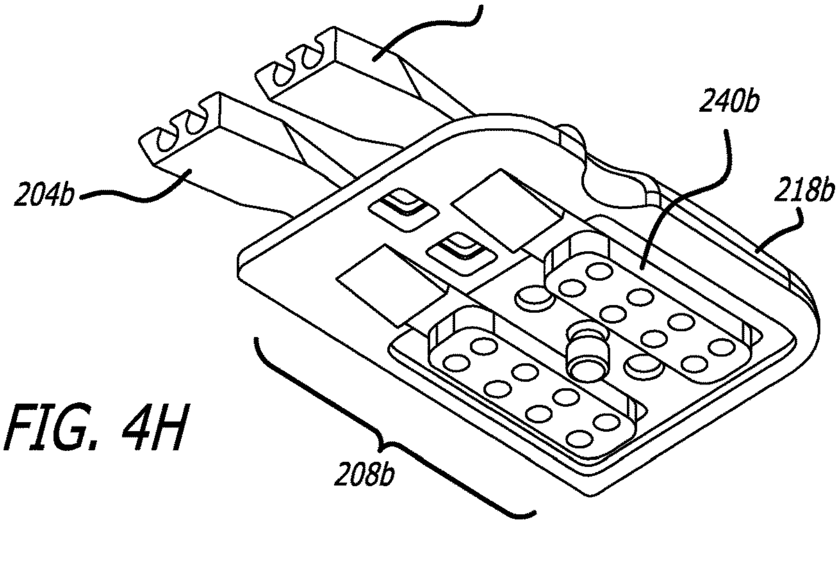
Figure 4I:
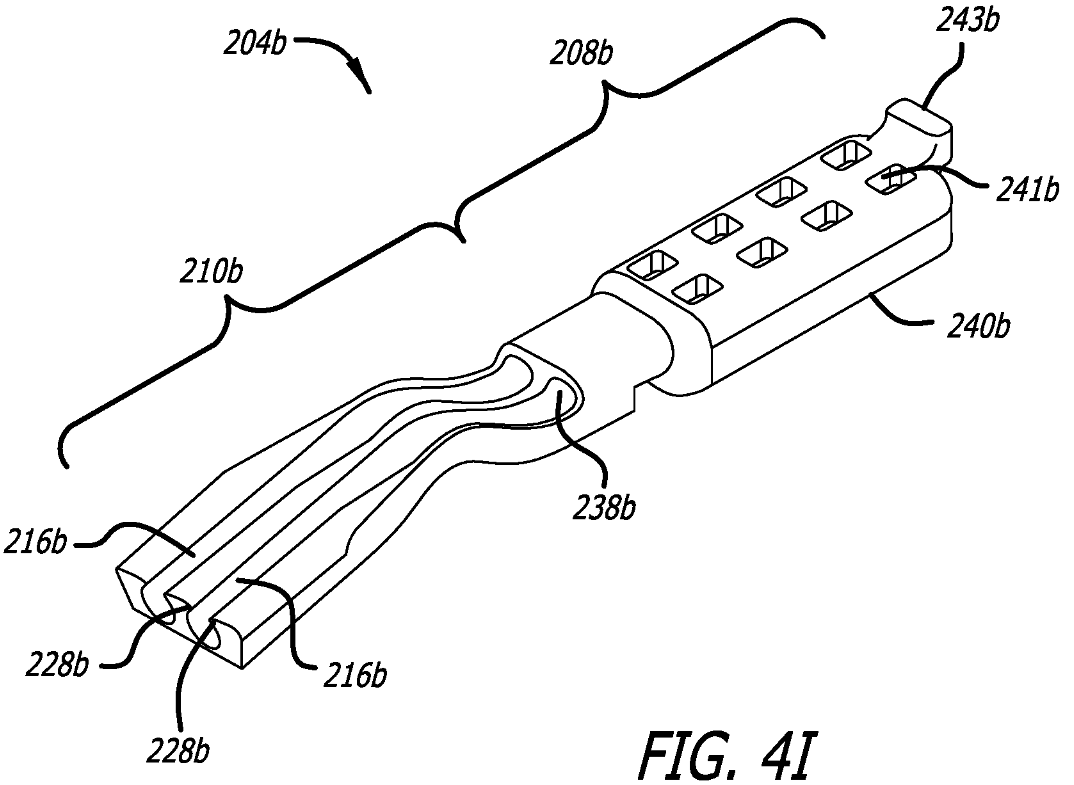
FIG. 4I is an illustration of a lower strain relief of the neurostimulator of FIG. 4A.

With reference to FIGS. 4G-4I, each of the lower strain reliefs 204*b* include a seal portion 208*b* and a strain relief portion 210*b*. The seal portion 208*b* includes a pair of ports 238*b* (see FIGS. 4G and 4J), each configured to receive a connector end of a lead 224*b*. The seal portion 208*b* also includes a footing 240*b* (see FIGS. 4H and 4J) having a plurality of openings 241*b*. As shown in FIG. 4E, the strain relief portion 210*b* extends away from the seal portion 208*b* and ramps up to a level above the bone table 212. The strain relief portion 210*b* then angles downward toward the bone table 212.

The strain relief portions 210*b* are open on top and includes a pair of channels 216*b*. During implant, a portion of a lead body is placed into a channel 216*b* of the strain relief portion 210*b* and the connector end of the leads 224*b* is inserted into a port 238*b* of the seal portion 208*b*. The channels 216*b* guide the connector ends of the leads into the ports 238*b* and make lead connection easier. The widths of these channels 216*b* generally correspond to the diameter of the lead body to thereby allow for easy placement of the lead body in, and removal of the lead body from, the lower strain reliefs 204*b*. The channels 216*b*, however, do include a reduced width section or overhanging features 228*b* that retain the lead body in place. The lead body is thereby retained in the lower strain relief 204*b* to minimize movement of the lead while other leads are being inserted into the ports 238*b* and to prevent the leads from moving during subsequent assembly of the cover assembly 206*b* to the can 214*b*. The cover assembly 206*b* includes a housing 218*b* with a pair of mating features 226*b* for engaging the upper strain relief 202*b*, and a coupling mechanism 236*b* like that described above with reference to FIGS. 2G and 2H.

The lower strain reliefs 204*b* and the housing 218*b* of the cover assembly 206*b* include respective coupling features 243*b*, 245*b* that mechanically couple the components together. For example, the lower strain reliefs 204*b* may include a retaining protrusion 243*b* at its proximal end that mates with a retaining opening 245*b* at the proximal end of the housing 218*b*. The location of the retaining protrusion 243*b* is not limited to the proximal end of the lower strain relief and may be located anywhere along the top edge of the footing 240*b*. The mechanical coupling between the lower strain reliefs 204*b* and the housing 218*b* prevents separation of the components before, during and after implant of the neurostimulator 200*b*, including during explant or replacement of the neurostimulator. The coupling feature 243*b* is positioned away from the footing 240*b* of the lower strain relief 204*b* to minimize disruption to the uniformity of the seal pressure when the cover assembly 206*b* is connected to the can 214*b*.

With reference to FIGS. 4B, 4C, and 4D, the upper strain relief 202*b* includes two channels 222*b* in its underside. Each of these channels 222*b* is sized to receive a lower strain relief portion 210*b*. The upper strain relief 202*b* includes additional features that retain the lower strain relief portions 210*b* in place within the channels 222*b*. These features include angled or tapered sidewalls, referred to herein as undercut features 225*b*, that mirror corresponding undercut features 227*b* of the lower strain relief portions 210*b*, and overbite features 231*b* that extend beyond the terminal ends 233*b* of the lower strain relief portions 210*b*. The upper strain relief 202*b* thus, in essence, wraps around and beyond the lower strain reliefs 204*b* (except for their underneath surfaces) and fills the space between the lower strain reliefs to thereby present a substantially continuous underneath surface (as best seen in FIG. 4B) that rests onto of the bone table 212*b* and thus, minimizes the formation of fibrotic tissue around the lower strain reliefs. The respective undercut features 225*b*, 227*b* aid in fixing the upper strain relief 202*b* to the lower strain reliefs 204*b*, whole the overbite features 231*b* improve the stiffness of the upper strain relief 202*b* and provide additional protection of the leads from the scalp at the point where the leads exit the lower strain relief.

With continued reference to FIGS. 4A-4J, part 220*b* of the housing 218*b* of the cover assembly 206*b* extends around and underneath the strain relief portions 210*b* to help support the strain relief portions. This part 220*b* of the housing 218*b* also helps lift the strain relief portions 210*b* up when the cover assembly 206*b* is being removed from the can 214*b* during can replacement.

With reference to FIGS. 4D and 4E, the channels 216*b* in the lower strain reliefs 204*b* may be formed to include a diameter that is slightly larger than the diameter of the portion of the lead 224*b* intended to be placed in the channel. As such, there is a space or clearance 235*b* between the lead 224*b* and the wall defining the channel 216*b*. The curvature 237*b* of the lower strain reliefs 204*b* imparts a corresponding curvature to the lead 224*b*. This curvature 237*b* provides sufficient retention to aid a physician in restricting movement of the lead 234*b* during the implant procedure.

With reference to FIG. 4F, the upper strain relief 202*b* includes one or more coupling features 225*b* configured to mate with corresponding coupling features 226*b* associated with the cover assembly 206*b*. When the upper strain relief 202*b* is pushed onto the cover assembly 206*b*, these coupling features 225*b*, 226*b* engage to position and retain the upper strain relief in place on the cover assembly.

Having described the structure of a second embodiment of a neurostimulator 200*a*, 200*b* having a strain relief system, procedures related to initial neurostimulator implant and neurostimulator can replacement are now described. While the following description is with reference to the first configuration of the neurostimulator 200*a*, the procedures for implant and replacement of the second configuration of the neurostimulator 200*b* are substantially the same.

With reference to FIGS. 3A-3G, during initial implant of the second embodiment of a neurostimulator 200*a*, the neurostimulator can 214*a* is secured within a ferrule implanted in a patient's cranium using known techniques. For example, a ferrule tab may be bent over the top of the can 214*a* to secure it in place. The distal, electrode-bearing ends of one or more leads 224*a* are implanted in the brain using known techniques. Proximal portions of the one or more leads 224*a* extend from a hole in the skull and are secured in place at the surface or bone table 212 of the skull using, for example, a burr hole cover.

With reference to FIG. 3C, a portion of each of the one or more leads (not shown) near the connector end of the lead is placed in a corresponding channel 216*a* of a lower strain relief 204*a*. The connector end of each of the one or more leads is then inserted into a corresponding tubular insert

238*a* of the cover assembly 206*a* and fully seated. Marker bands on the leads are used to indicate when a lead 224*a* is fully seated.

Figure 3E:
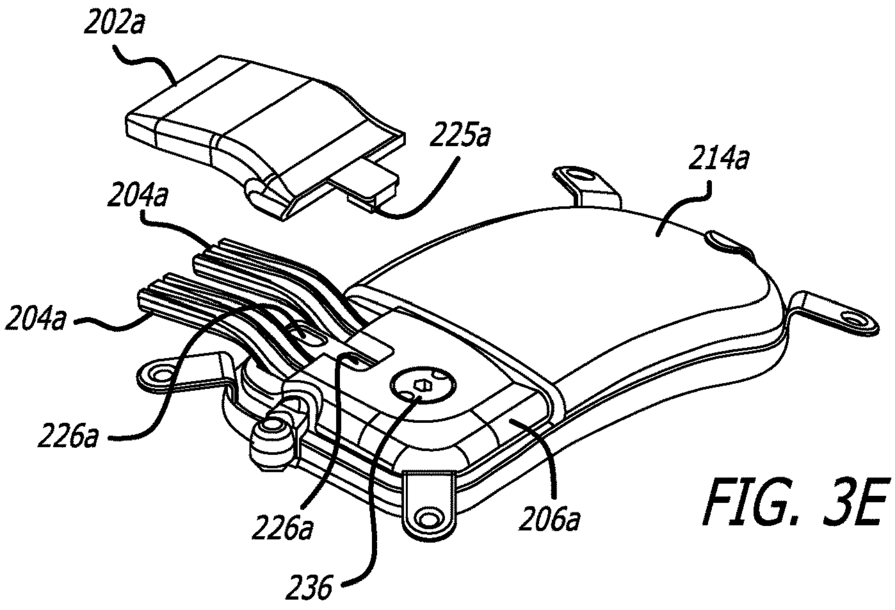
FIG. 3E is an illustration of the neurostimulator of FIG. 3A from a different perspective, partially disassemble to show the upper strain relief separated from the other components of the neurostimulator.

With reference to FIGS. 3B and 3E, the cover assembly 206*a* is mechanically and electrically coupled to the can 214*a*. To this end, the cover assembly 206*a* is placed in position over the can 214*a* and the undersides of the lower strain relief 204*a* is placed on the bone table. The footings 240*a* of the cover assembly 206*a* are then mated with the contact recesses 242*a* of the can 214*a* and the cover assembly is fully secured to the can 214*a* using the coupling mechanism 236*a*. A ferrule clamp may also be used to further secure the cover assembly.

With reference to FIGS. 3E, 3F and 3G the upper strain relief 202*a* is then placed over the lower strain reliefs 204*a* to align each respective channel 222*a* of the upper strain relief with a lower strain relief portion 210*a*. The upper strain relief 202*a* is coupled to the housing 218*a* of the cover assembly 206*a* and the lower strain relief 204*a* through respective coupling features 225*a*, 226*a*. These coupling features include, for example, one or more tabs 225*a* of the upper strain relief 202*a* and one or more corresponding holes 226*a* of the cover assembly 206*a*.

With reference to FIG. 3A-3G, during a can 214*a* replacement procedure, a surgical opening is created through the scalp, near the cover assembly 206*a* end of the neurostimulator 200*a*. The opening is large enough to expose the cover assembly 206*a*, the upper strain relief 202*a* and the portions of the leads 224*a* extending through the strain relief system 202*a*, 204*a* from the cover assembly.

With reference to FIG. 3A, the cover assembly 206*a* with integrated lower strain reliefs 204*a* is decoupled from the can 214*a* by loosening the coupling mechanism 236*a*. The cover assembly 206*a* with integrated lower strain reliefs 204*a*, and with the upper strain relief 202*a* still coupled to it, is then pulled away from the can 214*a* in the direction of the lower strain reliefs 204*a*. In doing so, the upper strain relief 202*a*, the lower strain reliefs 204*a* and the portions of the leads 224*a* retained in the strain reliefs are displaced from the surgical field surrounding the can 214*a*. Note: the upper strain relief 202*a* may be removed prior to pulling the cover assembly 206*a* away from the can 214*a*.

The can 214*a* is then removed from the ferrule by removing a ferrule clamp and sliding the can out from under the bent ferrule tab by lifting the recessed end of the can up slightly and pulling the can out in the direction of where the ferrule clamp was located. A new can 214*a* is placed and secured in the ferrule using the ferrule clamp and the ferrule tab. Then appropriate steps of the initial implant procedure described above are performed to complete the can replacement procedure.

Thus disclosed is a second embodiment of implantable medical device 200*a*, 200*b* configured for implant in a hole in cranium of a patient, relative to a bone table 212*a*, 212*b* corresponding to a surface of the cranium adjacent the hole. The implantable medical device 200*a*, 200*b* includes a can 214*a*, 214*b* having an electrical-contact pad 215*a*. The can 214*a*, 214*b* is characterized by a form factor having a perimeter edge 217*a*, 217*b* defining a boundary of the can, and a recessed portion 219*a* with an upper surface 227*a* positioned to lie beneath the bone table 212 when the can is placed in the hole, and that supports the electrical-contact pad 215*a*. The implantable medical device 200*a*, 200*b* also includes a cover assembly 206*a*, 206*b* having a plurality of ports 238*a*, 238*b*, each configured to receive a connector end of a lead 224*a*, 224*b*. The cover assembly 206*a*, 206*b* is configured to couple to the can 214*a*, 214*b* and decouple from the can at the electrical-contact pad 215*a*. The implantable medical device also includes a strain relief system that includes a lower strain relief 204*a*, 204*b* and an upper strain relief 202*a*, 202*b*. The lower strain relief 204*a*, 204*b* defines a plurality of channels 216*a*, 216*b*, each configured to receive a portion of a lead 224*a*, 224*b* body, and includes a curved portion 223*a*, 223*b* and a generally linear portion 265*a*, 265*b*. The curved portion 223*a*, 223*b* extends upward from a proximal end 261*a*, 261*b* at or near the upper surface 227*a* of the recessed portion 219*a* to a distal end 263*a*, 263*b* at the bone table 212. The generally linear portion 265*a*, 265*b* extends from the distal end 263*a*, 263*b* of the curved portion to a terminal end 233*a*, 233*b* beyond the perimeter edge 217*a*, 217*b* of the can 214*a*, 214*b*. The upper strain relief 202*a*, 202*b* is configured to mechanically couple to and mechanically decouple from one or both of the cover assembly 206*a*, 206*b* and the lower strain relief 204*a*, 204*b*. The upper strain relief 202*a*, 202*b* covers the plurality of channels 216*a*, 216*b* of the lower strain relief 204*a*, 204*b*.

In this embodiment, the lower strain relief 204*a*, 204*b* extends from the cover assembly 206*a*, 206*b* instead of extending from the can, as it does in other embodiments disclosed herein. The lower strain relief 204*a* may be integral with the cover assembly 206*a*. Integral in this context means that the lower strain relief 204*a* cannot be disassembled or removed from the cover assembly 206*a* without damaging the structural integrity of one or more of the component parts. In another configuration, the lower strain relief 204*b* is securely coupled to the cover assembly 206*b*. Securely coupled in this context means that the lower strain relief 204*a* can be disassembled or removed from other components of the cover assembly 206*b* without damaging the structural integrity of one or more of the component parts. To this end, the cover assembly 206*b* includes a housing 218*b* and the lower strain relief 204*b* extends from a footing 240*b* that is configured to mechanically couple to and mechanically decouple from the housing through corresponding coupling features 243*b*, 245*b*. With reference to FIGS. 3F and 3G, in one configuration, each of the upper strain relief 202*a*, and the lower strain relief 204*a* extends beyond the perimeter edge 217*a* of the can 214*a* a same distance. With reference to FIGS. 4B and 4C, in another configuration, the lower strain relief 204*b* extends beyond the perimeter edge 217*b* of the can 214*b* a distance less than the upper strain relief 202*b* and the upper strain relief includes a plurality of overbite features 231*b* that extend inward in front of the terminal end 233*b* of the lower strain relief 204*b*.

The objective of the second embodiment of the neurostimulator 200*a*, 200*b* is to facilitate easier can 214*a*, 214*b* replacement procedures. During can 214*a*, 241*b* replacement, the cover assembly 206*a*, 206*b* with the upper strain relief 202*a*, 202*b* and the lower strain reliefs 204*a*, 204*b* (and connected leads) can be lifted from the can 214*a*, 214*b* and folded out of the way of the can, thereby allowing for better access to the can. The lower strain reliefs 204*a*, 204*b* that extend from the cover assembly 206*a*, 206*b* make lifting the cover assembly and leads up and away from the can 214*a*, 214*b* easier during can replacement. The upper strain relief 202*a*, 202*b* wraps around the strain relief portions 210*a*, 210*b* so as to minimize the formation of fibrotic tissue around the lower strain relief 204*a*, 204*b*. Furthermore, the lower strain reliefs 204*a*, 204*b* are able to accommodate more variation is the height of the bone table 212 relative to the top surface of the can 214*a*, 214*b*, because the lower strain relief is not attached (fixed) to the can immediately adjacent to the bone table.

Strain Relief System with Independent Lower Strain Relief

With reference to FIGS. 5C-5G, in a third embodiment, a neurostimulator 300 includes a strain relief system having an upper strain relief 302 and a lower strain relief 304, each of which is independent of a can 314 of the neurostimulator 300. The strain relief system functions to secure leads 330 in place relative to the bone table 312 and to provide a smooth transition for the leads from the surface of the bone table down to the cover assembly 306, where the connector ends of the leads mechanically and electrically couple with the can 314 of the neurostimulator 300.

Figure 5A:
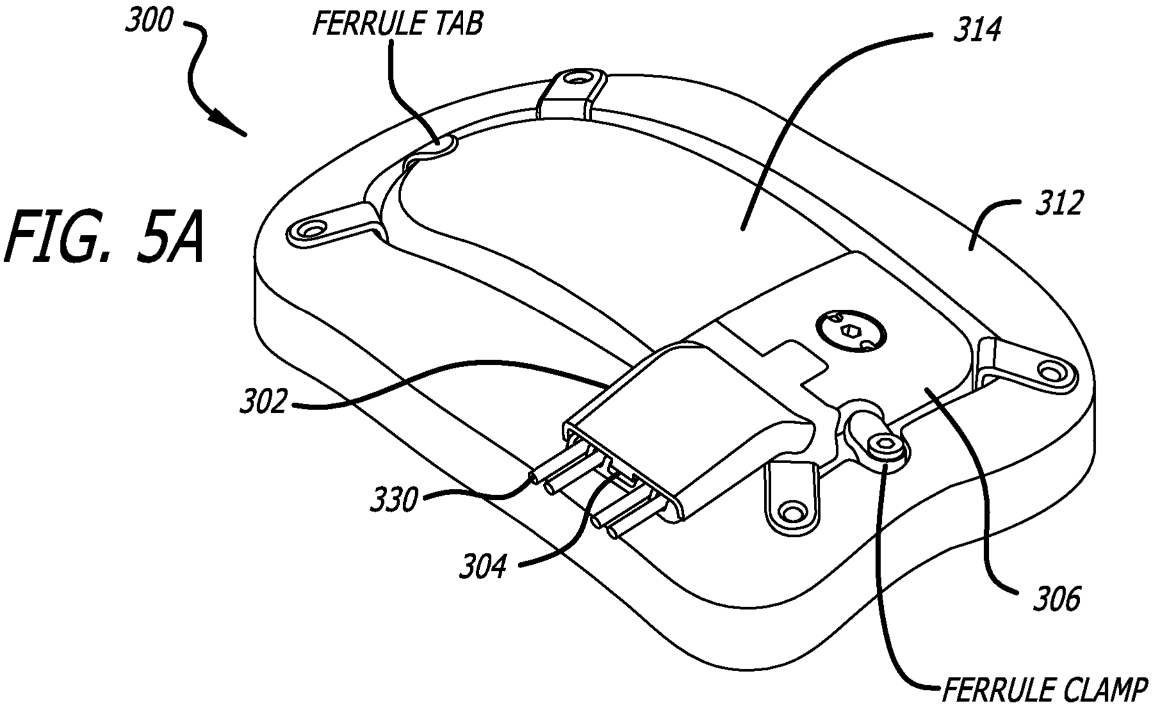
FIG. 5A is an illustration of a neurostimulator placed in a patient's cranium and having a strain relief system that includes an upper strain relief and a lower strain relief, each of which is independent of the neurostimulator can.
Figure 5B:
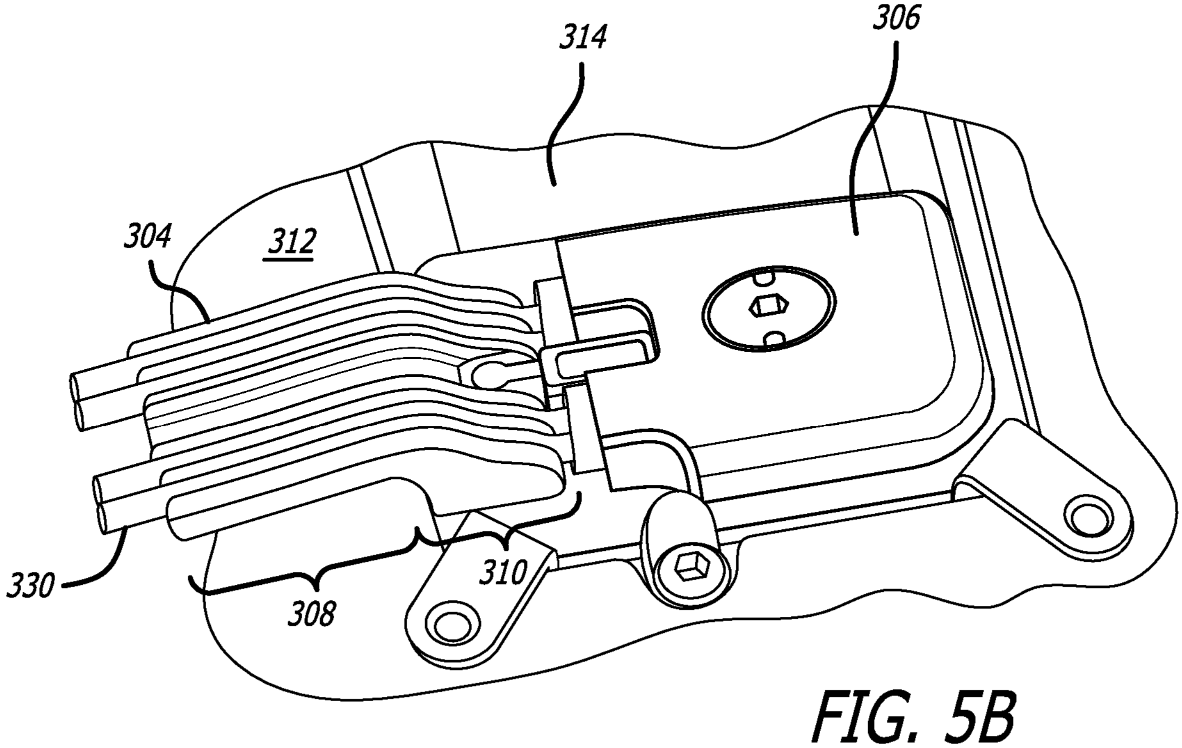
FIG. 5B is an illustration of an end of the neurostimulator of FIG. 5A.

As shown in FIG. 5B the lower strain relief 304 includes a first portion, referred to herein as a bone-table portion 308, and a second portion, referred to herein as a can portion 310. When the neurostimulator 300 is implanted, the bone-table portion 308 extends from the edge of the can 314 over the bone table 312, while the can portion 310 rests on a recessed portion of the can. The lower strain relief 304 is configured and positioned relative to the can 314 such that the underside of the bone-table portion 308 of the lower strain relief lies in a plane that generally aligns with the top surface of the can 314. As such, upon implant of the neurostimulator 300 the underside of the bone-table portion 308 of the lower strain relief sets down on the patient's bone table 312.

Figure 5C:
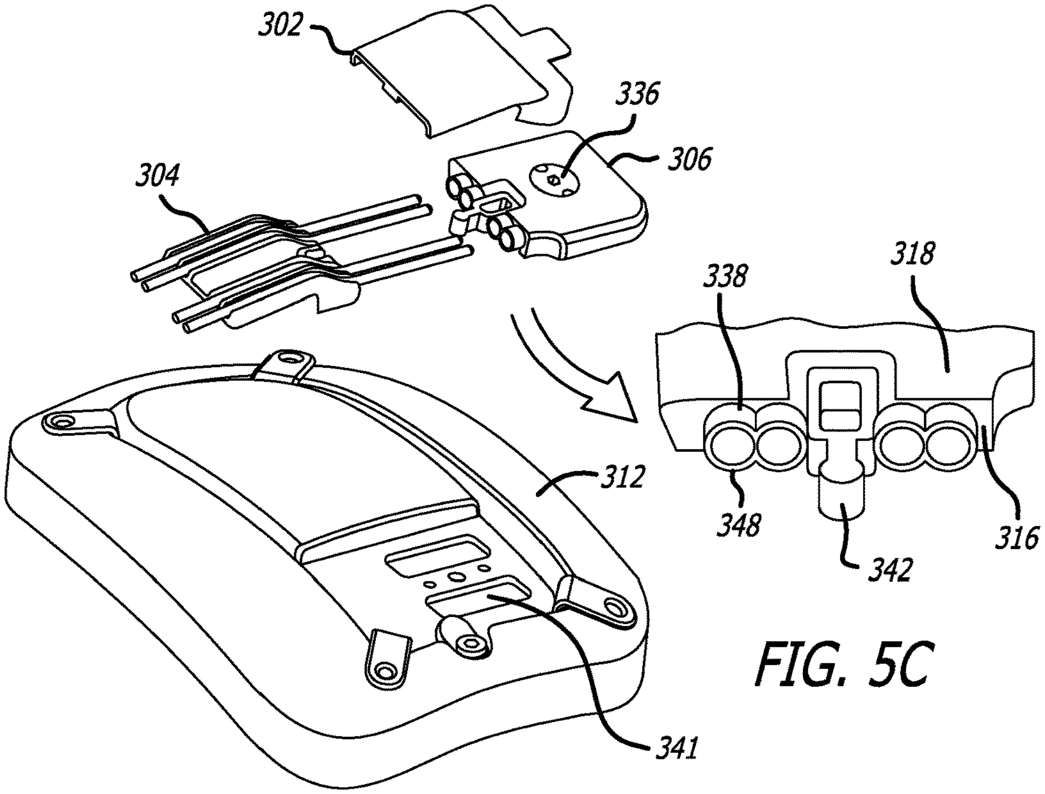
FIG. 5C is an illustration of the neurostimulator of FIG. 5A, partially disassembled to show components of the neurostimulator including the upper strain relief, the lower strain relief, and a cover assembly.
Figure 5D:
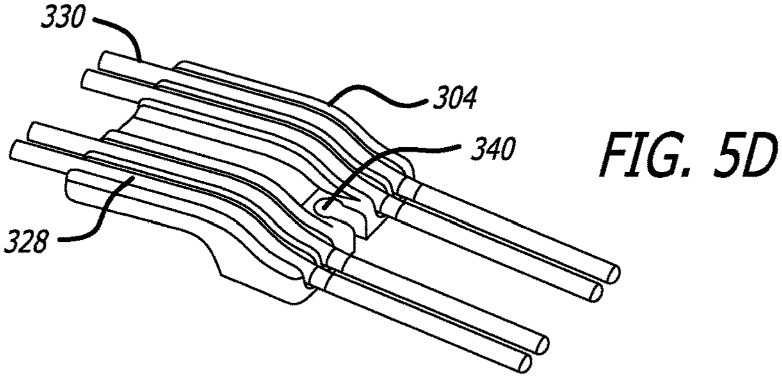
FIGS. 5D and 5E are illustrations of leads placed in the lower strain relief of FIG. 5A from different perspectives.
Figure 5E:
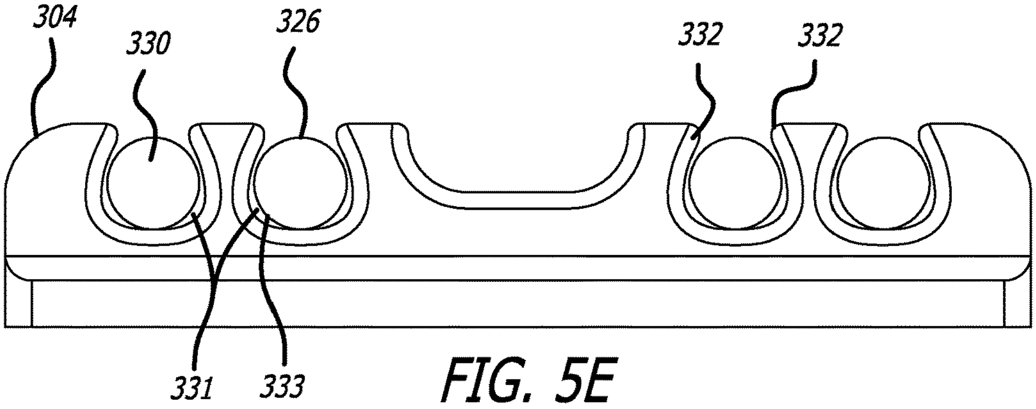

With reference to FIGS. 5D and 5E, the lower strain relief 304 is configured to retain two pairs of leads 330. To this end, the lower strain relief includes channels 326 for receiving a portion 328 of a lead 330 to secure and retain the lead in place. The channels 326 include a reduced width section or overhanging features 332 that retain the leads in place. The shape of the channels in the lower strain relief 304 retain the lead, however the shape avoids intimate surface to surface contact that would promote cohesion between the lead and the lower strain relief over prolonged contact. To this end, there are gaps 331 between the surfaces defining the channels 326 and the surfaces 333 of the lead body. The lead 330 would be difficult to remove if it was adhered to the lower strain relief 304. The lower strain relief 304 includes a coupling feature 340, e.g., a cutout. The lower strain relief 304 may be made of silicone.

Figure 5F:
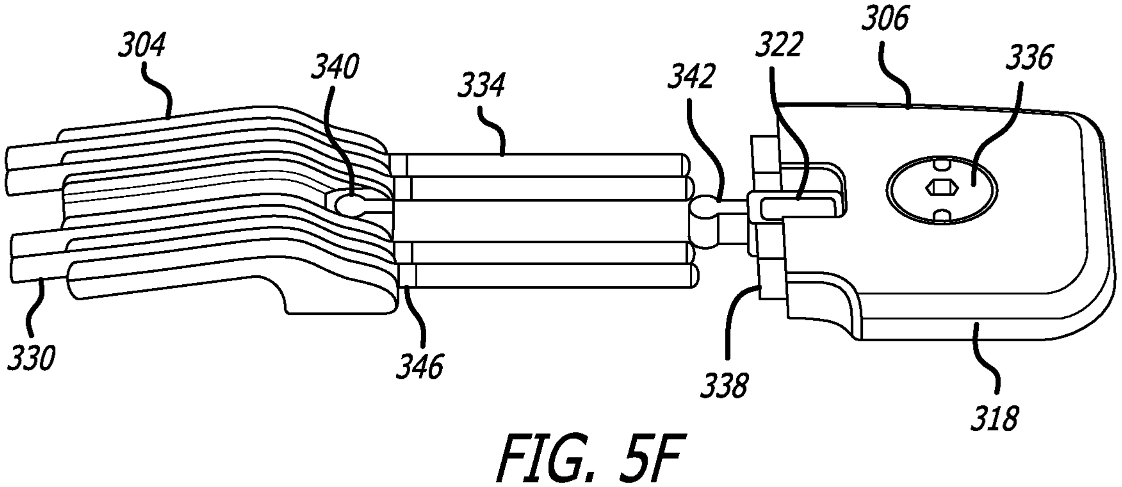
FIG. 5F is an illustration of leads placed in a lower strain relief of the neurostimulator of FIG. 5A and aligned for insertion into a cover assembly.
Figure 5G:
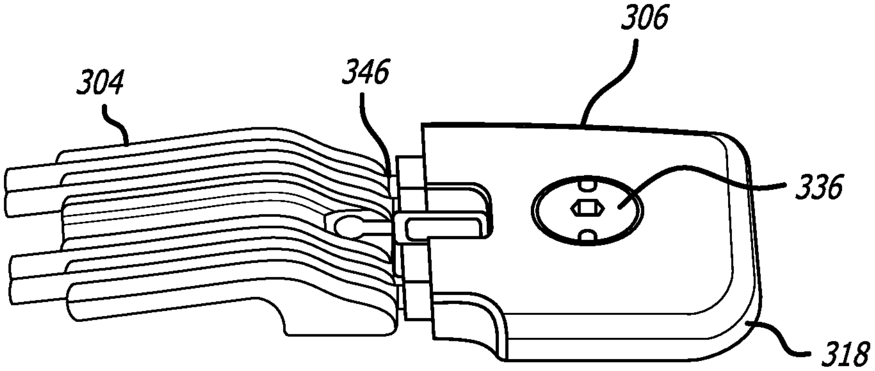
FIG. 5G is an illustration of the leads and lower strain relief shown in FIG. 5F inserted into and coupled with the cover assembly.

With reference to FIGS. 5F and 5G, the cover assembly 306 includes a housing 318 with a coupling feature 342 configured to engage the coupling feature 340 of the lower strain relief 304. The coupling features 340, 342 at the center of the housing and the lower strain relief 304 lock the two components together as a single assembly. The cover assembly 306 also includes a mating feature 322 configured to engage a corresponding feature of the upper strain relief 302. The cover assembly 306 also includes a coupling mechanism 336 like that described above with reference to FIGS. 2G and 2H that secures the cover assembly to the can 314. The cover assembly 306 includes a seal like that described above with reference to FIGS. 2G and 2H, including an inlet region of the tubular inserts 338 that extends beyond the end 316 of the housing 318.

With reference to FIGS. 5F and 5G, once portions 328 of the leads 330 are placed in the lower strain relief 304, the connector ends 334 of the leads are aligned with the tubular inserts 338 of the cover assembly 306. The connector ends 334 are then inserted into the tubular inserts 338 as a set until the connectors are fully seated. Marker bands 346 at the ends of the connectors indicate when the connectors are fully seated. With reference to FIG. 5C, the tubular inserts 338 extend beyond the end of the housing 318 of the cover assembly 306 and have an inner diameter that tapers outward toward their front end 348 to provide a larger diameter entry port to make insertion of the connector ends 334 into the inserts easier.

The upper strain relief 302 is configured similar to the upper strain relief of FIGS. 3E, 3F and 3G, and couples to the lower strain relief 304 and cover assembly 306 in the same way as described with reference to FIGS. 3E, 3F and 3G. The upper strain reliefs 302 may be made of silicone material either harder and stiffer or softer and more flexible than the lower strain relief 304.

Having described the structure of a third embodiment of a neurostimulator 300 having a strain relief system, procedures related to initial neurostimulator implant and neurostimulator can replacement are now described.

With reference to FIG. 5A-5G, during initial implant of the third embodiment of a neurostimulator 300, the neurostimulator can 314 is secured within a ferrule implanted in a patient's cranium using known techniques. For example, a ferrule tab may be bent over the top of the can 314 to secure it in place. The distal, electrode-bearing ends of one or more leads 330 are implanted in the brain using known techniques. Proximal portion of the one or more leads extend from a hole in the skull and are secured in place at the surface or bone table 312 of the skull using, for example, a burr hole cover.

With reference to FIGS. 5C and 5D, a portion 328 of each of the one or more leads 330 is placed in a corresponding channel 326 of the lower strain relief 304. The connector end 334 of each of the one or more leads 330 is fully seated into a corresponding tubular insert 338 of the cover assembly 306 as a set (all at the same time). While seating the connector ends 334 of the one or more leads 330, the lower strain relief 304 is mechanically coupled to cover assembly through respective features 340, 342. Marker bands 346 on the leads are used to indicate when a lead is fully seated. The upper strain relief 302 is then placed over the lower strain relief 304 and is coupled to lower strain relief and the cover assembly 306 and the lower strain relief 304 by various mating features. Note, the cover assembly 306 may be secured to the can 314 before the upper strain relief is coupled to the lower strain relief and the cover assembly.

With reference to FIG. 5B, the cover assembly 306 is mechanically and electrically coupled to the can 314. To this end, the cover assembly 306 is placed in position over the can 314 and the undersides of the upper and lower strain reliefs are placed on the bone table 312. The footings on the underside of the cover assembly 306 are then mated with the contact recesses 341 of the can 314 and the cover assembly is fully secured to the can 314 using the coupling mechanism 336. A ferrule clamp may also be used to further secure the cover assembly.

With reference to FIGS. 5A-5G, during a can 314 replacement procedure, a surgical opening is created through the scalp near the cover assembly 306 end of the neurostimulator 300. The opening is large enough to expose the cover assembly 306, the upper strain relief 302 and the portions of the leads 330 extending from the cover assembly.

With reference to FIG. 5A, the cover assembly 306 is decoupled from the can 314 by loosening the coupling mechanism 336. The cover assembly 306 with the upper strain relief 302 still coupled to it, is then pulled away from the can in the direction of the lower strain relief 304. In doing so, the upper strain relief 302, the lower strain relief 304 and the portions 328 of the leads retained in the strain reliefs are displaced from the surgical field surrounding the can 314. Note: the upper strain relief 302 may be removed prior to pulling the cover assembly 306 away from the can 314.

The can 314 is then removed from the ferrule by removing a ferrule clamp and sliding the can out from under the bent ferrule tab by lifting the recessed end of the can up slightly and pulling the can out in the direction of where the ferrule clamp was located. A new can 314 is placed and secured in the ferrule using a ferrule clamp and the ferrule tab. Then appropriate steps of the of the initial implant procedure described above are performed to complete the can replacement procedure.

The objective of the third embodiment of the neurostimulator 300 is to facilitate easier can replacement procedures. During can 314 replacement, the cover assembly 306 with the upper strain relief 302 and the lower strain relief 304 (and connected leads) could be lifted from the can 314 and folded out of the way of the can, thereby allowing for better access to the can.

Strain Relief System with Removable Lower Strain Relief

With reference to FIGS. 6A-6E, in a fourth embodiment, a neurostimulator 400 includes a strain relief system having an upper strain relief 402 and a lower strain relief 404 that is removable from a can 414 of the neurostimulator 400. The lower strain relief 404 is configured to be placed partially in the can 414 and removably coupled thereto, while also partially extending over the bone table 412. The lower strain relief 404 can be placed in and removed from its position as needed to facilitate implant and replacement. The strain relief system functions to secure leads in place relative to the bone table 412 and to provide a smooth transition from the bone table to the cover assembly 406, where the connector ends of the leads mechanically and electrically couple with the can 414 of the neurostimulator 400.

As shown in FIG. 6D the lower strain relief 404 includes a first portion, referred to herein as a bone-table portion 408, and a second portion, referred to herein as a can portion 410. When the neurostimulator 400 is implanted, the bone-table portion 408 extends from the edge of the can 414 over the bone table 412, while the can portion 410 rests on a recessed portion of the can. The lower strain relief 404 is configured and positioned relative to the can 414 such that the underside of the bone-table portion 408 of the lower strain relief lies in a plane that generally aligns with the top surface of the can 414. As such, upon implant of the neurostimulator 400 the underside of the bone-table portion 408 of the lower strain relief sets down on the bone table 412. This is beneficial as it minimizes the formation of fibrotic tissue in that space and makes can replacement easier.

With reference to FIG. 6A-6D, as noted above, the lower strain relief 404 is configured to be positioned partially in the can 414 and partially over the bone table 412 and is further configured to be attached in place to the can. To this end, the lower strain relief 404 includes one or more coupling features 416, e.g., a hole, configured to mate with corresponding coupling features 418, e.g., a retention post, associated with the can 414. When the can portion 410 of the lower strain relief 404 is pushed onto the can 414, these coupling features 416, 418 engage to position and retain the lower strain relief in place. For example, the hole 416 in the lower strain relief 404*b* is configured to allow the relief to slip over the post 418 and be locked down onto the post. The lower strain relief 404 can be pushed onto and pulled off the can 414 as needed to facilitate implant and replacement. The can 414 may include additional pin features 424 that orient the lower strain relief 404 when assembled onto the can 414.

Figure 6A:
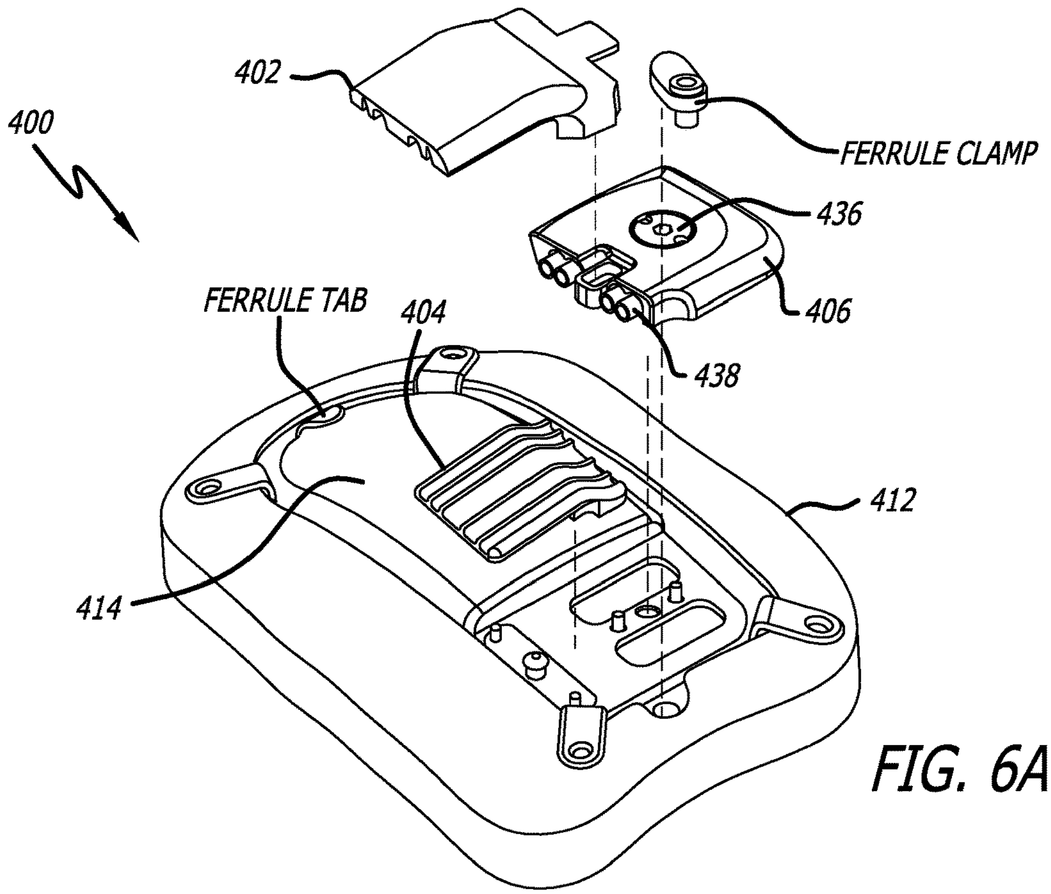
FIG. 6A is an illustration of a neurostimulator placed in a patient's cranium and having a strain relief system that includes an upper strain relief and a lower strain relief, disassemble to show a lower strain relief configured to be coupled to and decoupled from a can component of the neurostimulator.
Figure 6B:
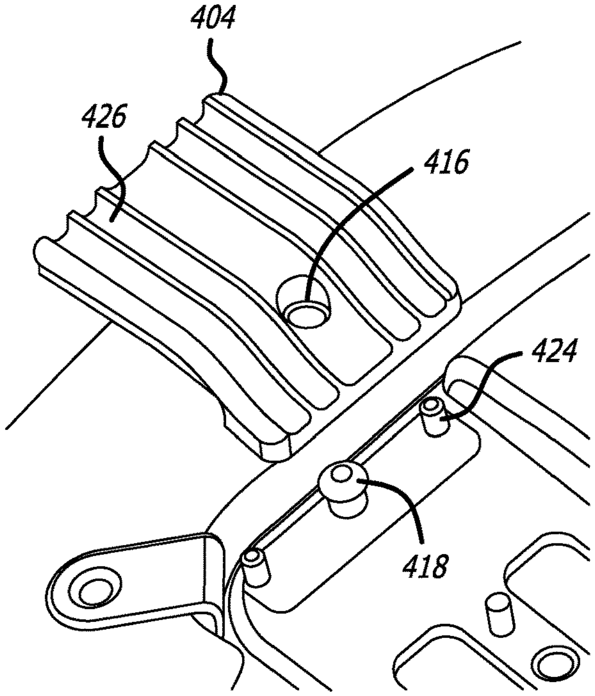
FIGS. 6B and 6C are illustrations of the lower strain relief of FIG. 6A from different perspectives.
Figure 6C:
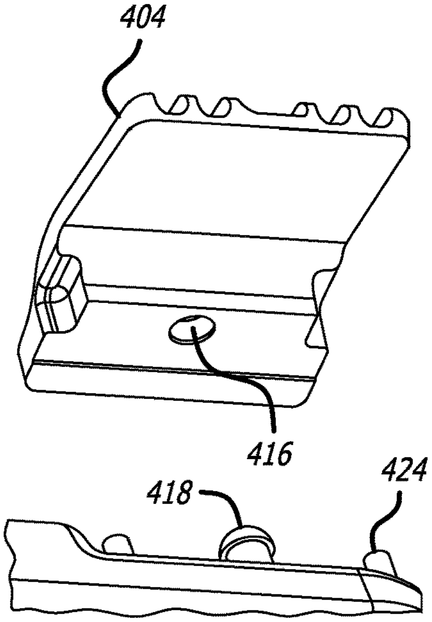

As shown in FIG. 6B, the lower strain relief 404 is configured to retain two pairs of leads. To this end, the lower strain relief 404 includes four channels 426 for receiving a portion of a lead to secure and retain the lead in place. The widths of these channels 426 generally correspond to the diameter of the lead body to thereby allow for easy placement of the leads in, and removal of the leads from, the lower strain relief 404. The channels 426 are free of any reduced width sections or overhanging features that would retain the lead in place and potentially interfere with easy removal of the leads from the lower strain relief 404, for example during a can 414 replacement procedure. The lower strain relief 404 may be made of silicone.

With reference to FIG. 6E, the upper strain relief 402 includes one or more features 420 configured to mate with corresponding features 422 associated with the cover assembly 406. When the upper strain relief 402 is pushed onto the cover assembly 406, these features 420, 422 engage to position and retain the upper strain relief in place on the cover assembly. The upper strain relief 402 includes two channel 428 on its underside that are sized and curved to mate with corresponding projections of the lower strain relief 404. The upper strain relief 402 is configured similar to the upper strain relief of FIGS. 3E, 3F and 3G, and couples to the lower strain relief 404 and cover assembly 406 in the same way as described with reference to FIGS. 3E, 3F and 3G. The upper strain reliefs 402 may be made of silicone material either harder and stiffer or softer and more flexible than the lower strain relief. The cover assembly 406 is the same as described above with reference to FIGS. 5A-5G.

Having described the structure of a fourth embodiment of a neurostimulator 300 having a strain relief system, procedures related to initial neurostimulator implant and neurostimulator can replacement are now described.

With reference to FIG. 6A-6E, during initial implant of the fourth embodiment of a neurostimulator 400, the neurostimulator can 414 is secured within a ferrule implanted in a patient's cranium using known techniques. For example, a ferrule tab may be bent over the top of the can 414 to secure it in place. The distal, electrode-bearing ends of one or more leads are implanted in the brain using known techniques. Proximal portions of the one or more leads extend from a hole in the skull and are secured in place at the surface or bone table 812 of the skull using, for example, a burr hole cover.

With reference to FIGS. 6A and 6B, a lower strain relief 404 is coupled to the can 414. The connector ends of each of the one or more leads is fully seated into a corresponding tubular insert 438 of the cover assembly 406. Marker bands on the leads are used to indicate when a lead is fully seated. The cover assembly 406 (with connected leads) is placed in position in the can 414 and a portion of each of the one or more leads is placed in a corresponding channel 426 of the lower strain relief 404. The cover assembly 406 is then fully secured to the can using the coupling mechanism 436. The upper strain relief 402 is then placed over the lower strain relief 404 and is coupled to lower strain relief and the housing of the cover assembly 406 and the lower strain relief 404 by various mating features.

With reference to FIGS. 6A-6E, during a can 414 replacement procedure, a surgical opening is created through the scalp near the cover assembly 406 end of the neurostimulator 400. The opening is large enough to expose the cover assembly 406, the upper strain relief 402 and the portions of the leads extending from the cover assembly.

The upper strain relief 402 is removed from the cover assembly 406 and the lower strain relief 404. The cover assembly 406 is decoupled from the can 414 by loosening the coupling mechanism 436. The cover assembly 406 is then pulled away from the can 414 in the direction of the lower strain relief 404. In doing so, the portions of the leads placed in the lower strain relief 404 are removed from the lower strain relief and are displaced from the surgical field surrounding the can 414. The lower strain relief 404 is then decoupled from the can 414.

The can 414 is then removed from the ferrule by removing a ferrule clamp and sliding the can out from under the bent ferrule tab by lifting the recessed end of the can up slightly and pulling the can out in the direction of where the ferrule clamp was located. A new can 414 is placed and secured in the ferrule using a ferrule clamp and the ferrule tab. Then appropriate steps of the of the initial implant procedure described above are performed to complete the can replacement procedure.

The objective of the fourth embodiment of the neurostimulator 400 is to facilitate easier can 414 replacement procedures. During can 414 replacement, removal of the lower strain relief 404 reduces the footprint of the surgical space near the can, thereby allowing for better access to the can.

Strain Relief System with Two-Part Lower Strain Relief

With reference to FIGS. 7A and 7B, in a fifth embodiment, a neurostimulator 500 includes a strain relief system having an upper strain relief 502 and a lower strain relief that is split into a distal part 504 and a proximal part 506. The distal part 504 is configured to be attached to cranium with bone screw. The proximal part 506 is configured to be attached to the can 514 or to be keyed and held down by a cover. The proximal part 506 may have lead retention features if attached to cover. The distal part 504 and the proximal part 506 of the lower strain relief may be made of silicone elastomer. The upper strain relief 502 may also be made of silicone elastomer During initial implant of a fifth embodiment of a neurostimulator 500, a neurostimulator can 514 with the proximal part 506 of the lower strain relief already secured to it is secured within a ferrule implanted in a patient's cranium using known techniques. For example, a ferrule tab may be bent over the top of the can 514 to secure it in place. The distal, electrode-bearing ends of one or more leads are implanted in the brain using known techniques. The one or more leads extend from a hole in the skull where they are secured in place at the surface or the bone table 512 of the skull using, for example, a burr hole cover. The proximal ends of one or more leads are tunneled under the scalp to the can site.

The connector ends of the leads 524 are inserted into the cover assembly 508. The cover assembly 508 with leads inserted is placed in position over the can 514 in the area of the electrical-contact pad 515, and a portion 528 of each of the one or more leads 524 is placed in a respective channel of the proximal part 506 of the lower strain relief. The cover assembly 508 is then fastened to the can 514 in the area of the electrical-contact pad 515 using a locking mechanism 536 associated with the cover assembly.

The distal part 504 of the lower strain relief is secured to the bone table 512 to align its channels with the channels of the proximal part 506. A portion of each of the one or more leads is placed in a respective channels of the distal part 504 of the lower strain relief. The upper strain relief 502 is then placed over the distal part 504 and the proximal part 506 of the lower strain relief and over an end portion of the cover assembly 508 and secured in place.

With reference to FIG. 7A, during a can 414 replacement procedure, a surgical opening is created through the scalp near the cover assembly 508 end of the neurostimulator 500. The opening is large enough to expose the cover assembly 508, the upper strain relief 502 and the portions 528 of the leads extending from the cover assembly.

The upper strain relief 502 is removed from the cover assembly 508 and the lower strain relief. The cover assembly 508 is then decoupled from the can 514, and pulled away from the can 514 so that the portions of the leads placed in the distal part 504 and the proximal part 506 of the lower strain relief are removed from their respective channels and are displaced from the surgical field surrounding the can 514.

The can 514, including the proximal part 506 of the lower strain relief, is then removed from the ferrule by removing a ferrule clamp and sliding the can out from under the bent ferrule tab by lifting the recessed end of the can up slightly and pulling the can out in the direction of where the ferrule clamp was located. A new can 514, including the proximal part 506 of the lower strain relief, is placed and secured in the ferrule using a ferrule clamp and the ferrule tab. Then appropriate steps of the of the initial implant procedure described above are performed to complete the can replacement procedure.

Strain Relief System with Hinged Lower Strain Relief

With reference to FIGS. 8A and 8B, in a sixth embodiment, a neurostimulator 600 includes a strain relief system having an upper strain relief 602 and a lower strain relief that includes a distal portion 604 and a proximal portion 606. The distal portion 604 and the proximal portion 606 are hinged together. As such, the proximal portion 606 may be lifted by hinge action to remove/replace device. The distal portion 604 is configured to be attached to the bone table 612 with a bone screw. The proximal portion 606 may be keyed and held down by a cover. The distal portion 604 and the proximal portion 606 of the lower strain relief may be made of silicone elastomer. The upper strain relief 602 may also be made of silicone elastomer During initial implant of a sixth embodiment of a neurostimulator 600, a neurostimulator can 614 is secured within a ferrule implanted in a patient's cranium using known techniques. For example, a ferrule tab may be bent over the top of the can 614 to secure it in place. The distal, electrode-bearing ends of one or more leads are implanted in the brain using known techniques. The one or more leads extend from a hole in the skull where they are secured in place at the surface or bone table 612 of the skull using, for example, a burr hole cover. The proximal ends of one or more leads are tunneled under the scalp to the device site.

The distal portion 604 of the lower strain relief is placed on the bone table 612 so as to locate the proximal portion 606 on the top surface of the recessed portion of the can. The connector ends of the leads 624 are inserted into the cover assembly 608. The cover assembly 608 with leads inserted are is placed in position over the can 614, and a portion 628 of each of the one or more leads 624 is placed in a respective channel of each of the distal portion 604 and the proximal portion 606 of the lower strain relief. The cover assembly 608 is then fastened to the can 614 using a locking mechanism 636 associated with the cover assembly.

The distal portion 604 of the lower strain relief is then secured to the bone table 612 with a screw. The upper strain relief 602 is then placed over the distal portion 604 and the proximal portion 606 of the lower strain relief and over an end portion of the cover assembly and secured in place.

With reference to FIG. 8A, during a can 614 replacement procedure, a surgical opening is created through the scalp near the cover assembly 608 end of the neurostimulator 600. The opening is large enough to expose the cover assembly 608, the upper strain relief 602 and the portions 628 of the leads 624 extending from the cover assembly.

The upper strain relief 602 is removed from the cover assembly 608 and the distal portion 604 and proximal portion 606 of the lower strain relief. The cover assembly 608 is then decoupled from the can 614, and lifted together with the proximal portion 606 of the lower strain relief, to rotate the proximal portion about its hinge. In doing so, the cover assembly 608 and the coupled leads are displaced from the surgical field surrounding the can 614.

The can 614 is then removed from the ferrule by removing a ferrule clamp and sliding the can out from under the bent ferrule tab by lifting the recessed end of the can up slightly and pulling the can out in the direction of where the ferrule clamp was located. A new can 614 is placed and secured in the ferrule using a ferrule clamp and the ferrule tab. The cover assembly 608, together with the proximal portion 606 of the lower strain relief, are rotate about the hinge and the cover assembly 608 is then fastened to the new can 614 using the locking mechanism 636 associated with the cover assembly. The upper strain relief 602 is then placed over the distal portion 604 and the proximal portion 606 of the lower strain relief, and over an end portion of the cover assembly and secured in place.

Strain Relief System with Sheathed Upper Strain Reliefs

With reference to FIGS. 9A-9D, in a seventh embodiment, a neurostimulator 700, 800 includes a strain relief system having a pair of upper strain reliefs 702, 802 in the form of sheaths, and a lower strain relief that is split into a distal part 704, 804 and a proximal part 706, 806. The sheath 702, 802 provide protection to the proximal ends of the leads. The proximal part 706, 806 of the lower strain relief is configured to be attached to the can 714 or keyed/held down by a cap 713, 813. In the configuration shown in FIGS. 9A and 9B, the distal part 704 of the lower strain relief is attached to the ferrule. In the configuration shown in FIGS. 9C and 9C, the distal part 804 of the lower strain relief is configured to be attached to cranium with bone screws. The distal part 704/804 and the proximal part 706/806 of the lower strain relief may be made of silicone elastomer. The sheath 702, 802 may also be made of silicone elastomer.

Figure 9A:
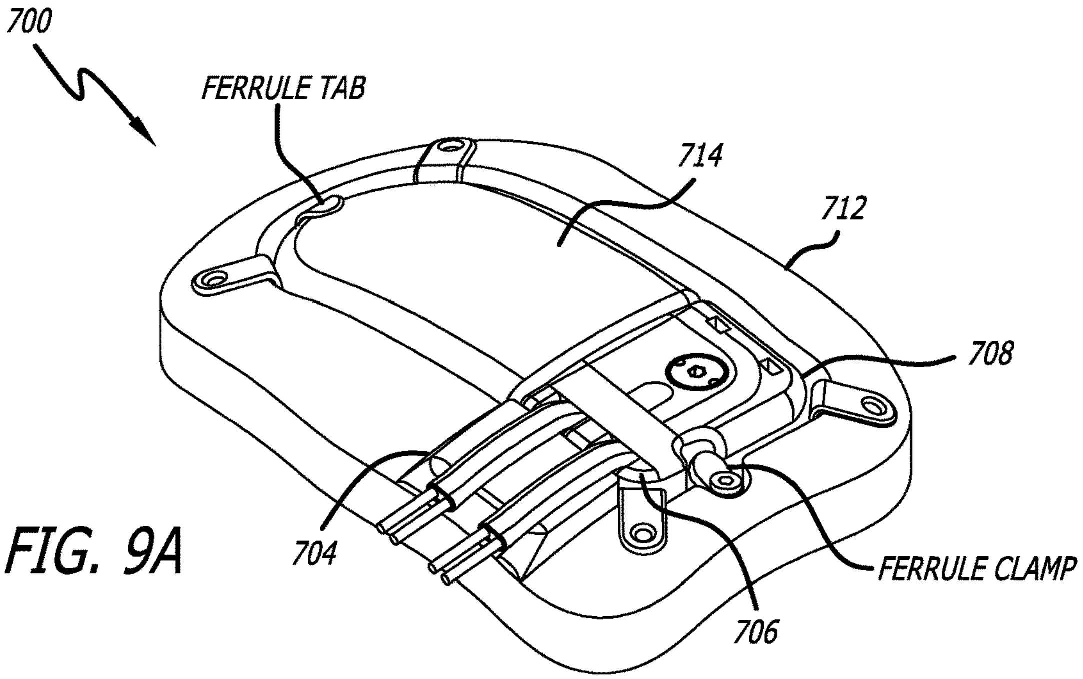
FIG. 9A is an illustration of a neurostimulator placed in a patient's cranium and having a strain relief system that includes a pair of protective sheaths and a lower strain relief that is split into a distal part and a proximal part.
Figure 9B:
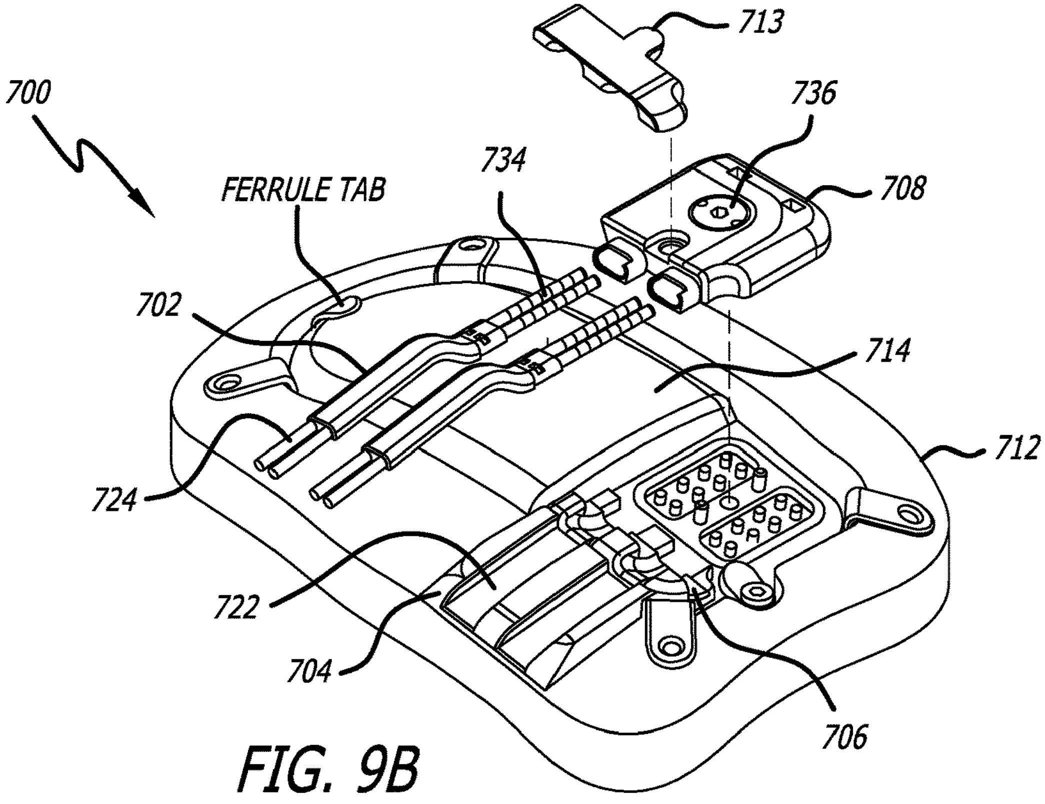
FIG. 9B is an illustration of the neurostimulator of FIG. 9A, disassembled to show a lower strain relief having a proximal part attached to a can of the neurostimulator and a distal part attached to a ferrule.
Figure 9C:
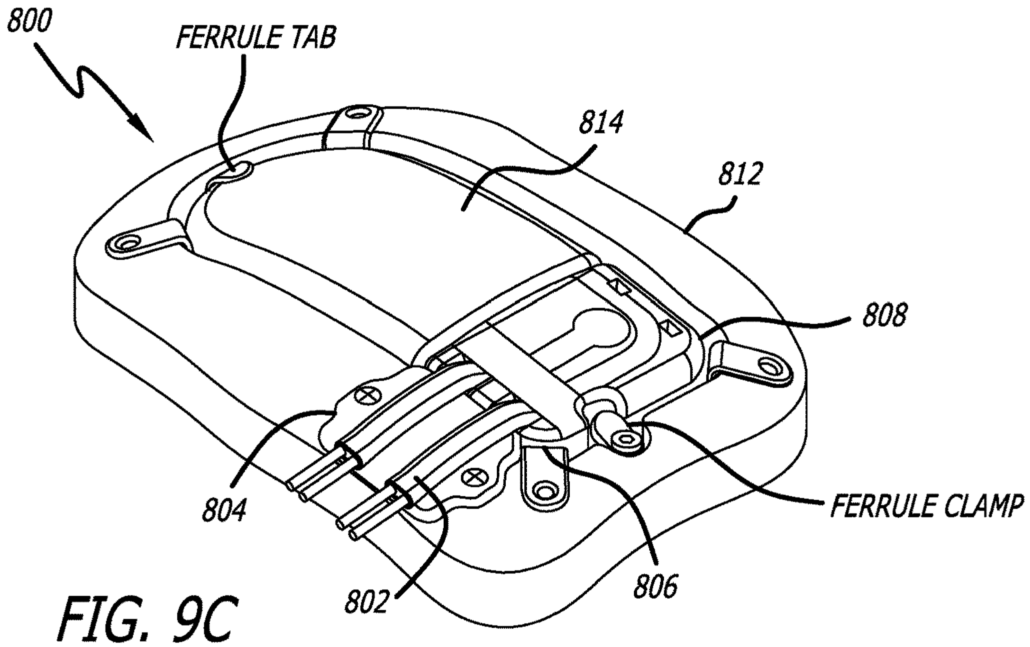
FIG. 9C is an illustration of a neurostimulator placed in a patient's cranium and having a strain relief system that includes a pair of protective sheaths and a lower strain relief that is split into a distal part and a proximal part.
Figure 9D:
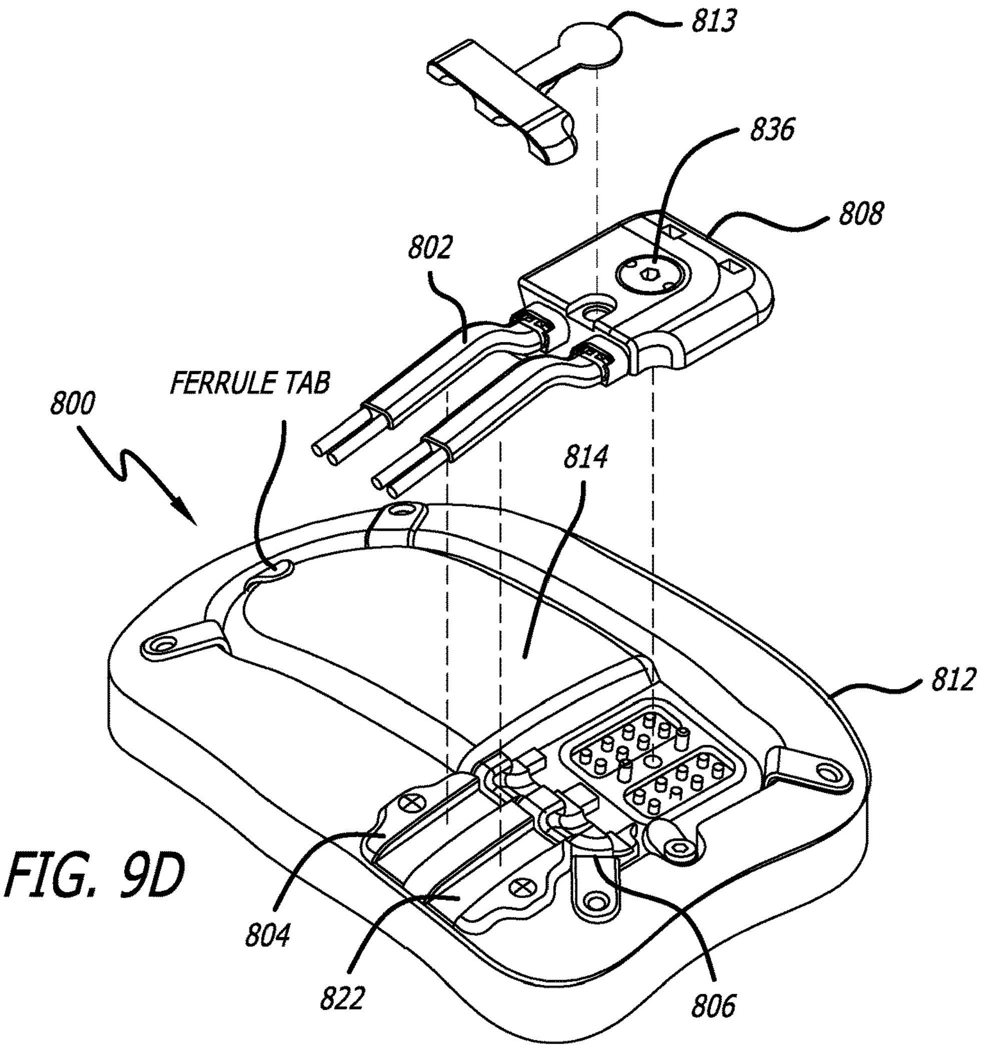
FIG. 9D is an illustration of the neurostimulator of FIG. 9C, disassembled to show a lower strain relief having a proximal part attached to a can of the neurostimulator and a distal part attached to the cranium.
Figure 9E:
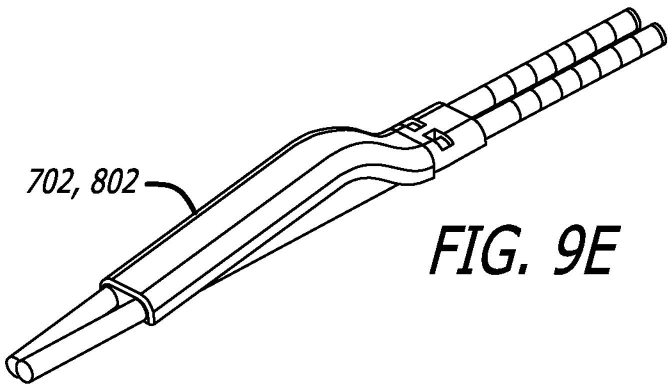
FIG. 9E is an illustration of a pair of leads being placed in a protective sheath of FIGS. 9C and 9D.
Figure 9F:
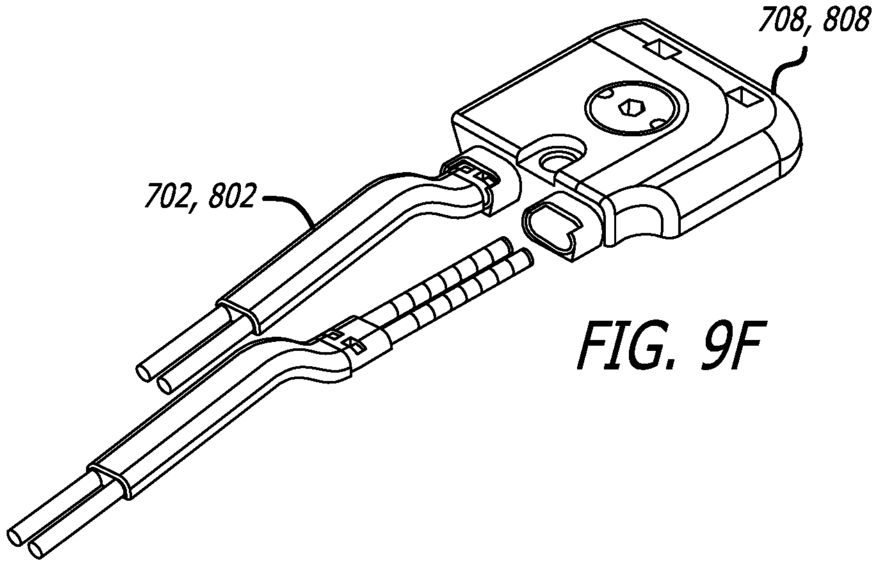
FIG. 9F is an illustration of leads in protective sheaths being coupled to a cover assembly.
Figure 9G:
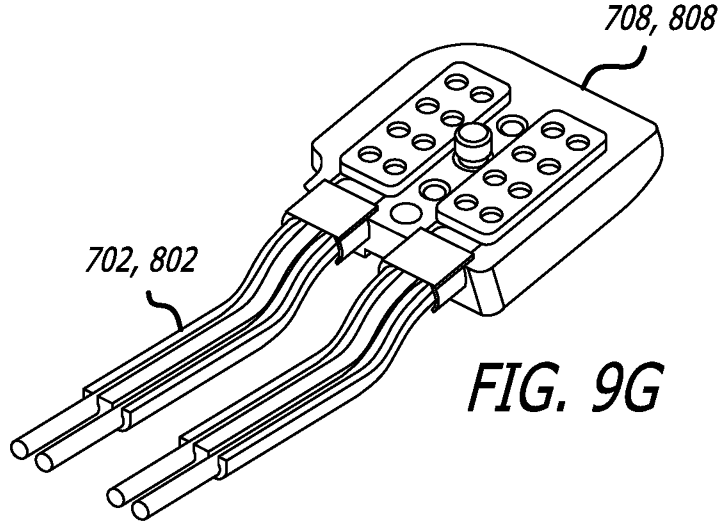
FIG. 9G is an illustration of the underside of the cover assembly of FIGS. 9B and 9D after the leads have been inserted.

With reference to FIGS. 9E-9G, during assembly of a neurostimulator 700, 800, a pair of leads is placed in a protective sheath 702, 802. The connector ends of the leads are then inserted into receptacles of the cover assembly 708, 808. As shown in FIG. 9G, the protective sheaths 702, 802 include channels configured to receive and retain the lead bodies. Alternatively, the sheath can have continuous circular lumens.

With reference to FIGS. 9A-9D, during initial implant of a seventh embodiment of a neurostimulator 700/800, a neurostimulator can 714/814 with a proximal part 706/806 of a lower strain relief, is secured within a ferrule implanted in a patient's cranium using known techniques. For example, a ferrule tab may be bent over the top of the can 614 to secure it in place. The distal, electrode-bearing ends of one or more leads 724 are implanted in the brain using known techniques. Proximal portions of the one or more leads extend from a hole in the skull and are secured in place at the surface or bone table 712 of the skull using, for example, a burr hole cover.

The distal part 704/804 of the lower strain relief is located on the bone table 612 of the cranium. In the configuration of the FIGS. 9A and 9B, the distal part is attached to the ferrule. In the configuration of the FIGS. 9C and 9D, the distal part is secured to the bone table 612. The connector ends 734 of the leads 724 are inserted into the cover assembly 708/808, as described above with reference to FIGS. 9E-9G.

The cover assembly 708/808 with leads inserted is then placed in position over the can 714/814, and each of the protective sheaths 702/802 is placed in a respective channels 722/822 of the distal part 704/804 and the proximal parts 706/806 of the lower strain relief. The cover assembly 708/808 is then fastened to the can 714/814 using a locking mechanism 736/836 associated with the cover assembly. The cap 713/813 is then placed over a portion of the proximal part 706/806 of the lower strain relief and an end portion of the cover assembly 708/808 and secured in place.

With reference to FIGS. 9A-9D, during a can 714/814 replacement procedure, a surgical opening is created through the scalp near the cover assembly 708/808 end of the neurostimulator 700/800. The opening is large enough to expose the cover assembly 708/808, the cap 713/813, and the protective sheaths 702/802 extending from the cover assembly.

The cap 713/813 is removed from the cover assembly 708/808. The cover assembly 708/808 is decoupled from the can 714/814. The cover assembly 708/808, with the leads still connected, is pulled away from the can 714/814 so that the portions of the protective sheaths 702/802 placed in channels 722/822 of the distal part 704/804 and proximal part 706/806 of the lower strain relief are removed and displaced from the surgical field surrounding the can 714/814.

The can 714/814 is then removed from the ferrule by removing a clamp and sliding the can out from under the bent ferrule tab by lifting the recessed end of the can up slightly and pulling the can out in the direction of where the ferrule clamp was located. A new can is placed and secured in the ferrule using a ferrule clamp and the ferrule tab. Then appropriate steps of the of the initial implant procedure described above are performed to complete the can replacement procedure.

In these embodiment, the distal part 704/804 of the lower strain relief does not have to be explanted during can replacement. The surgical field during can replacement is minimized and there is minimum exposure of leads to damage.

The various aspects of this disclosure are provided to enable one of ordinary skill in the art to practice the present invention. Various modifications to exemplary embodiments presented throughout this disclosure will be readily apparent to those skilled in the art. Thus, the claims are not intended to be limited to the various aspects of this disclosure, but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

What is claimed is:

1. An implantable medical device configured for implant in a hole in a cranium of a patient, relative to a bone table corresponding to a surface of the cranium adjacent the hole, the implantable medical device comprising:

a can having an electrical-contact pad, the can characterized by a form factor having a perimeter edge defining a boundary of the can, and a recessed portion with an upper surface positioned to lie beneath the bone table when the can is placed in the hole, and that supports the electrical-contact pad;

a cover assembly having a plurality of ports, each of the plurality of ports configured to receive a connector end of a lead, the cover assembly configured to couple to the can and decouple from the can at the electrical-contact pad; and a strain relief system comprising:

a lower strain relief defining a plurality of channels, wherein each of the plurality of channels is configured to receive a portion of a lead body and includes a curved portion that extends upward from a proximal end at or near the upper surface of the recessed portion to a distal end at the bone table, and an upper strain relief configured to cover the plurality of channels of the lower strain relief.

2. The implantable medical device of claim 1, wherein the lower strain relief further comprises a generally linear portion that extends from the distal end of the curved portion to a terminating end beyond the perimeter edge of the can.

3. The implantable medical device of claim 1, wherein upper strain relief is configured to mechanically couple to and mechanically decouple from the cover assembly.

4. The implantable medical device of claim 1, wherein upper strain relief is configured to mechanically couple to and mechanically decouple from the lower strain relief.

5. The implantable medical device of claim 1, wherein upper strain relief is configured to mechanically couple to and mechanically decouple from both of the cover assembly and the lower strain relief.

6. The implantable medical device of claim 1, wherein the lower strain relief is fixedly secured at the upper surface of the recessed portion and extends beyond the perimeter edge of the can a distance less than the upper strain relief.

7. An implantable medical device configured for implant in a hole in cranium of a patient, relative to a bone table corresponding to a surface of the cranium adjacent the hole, the implantable medical device comprising:

a can having an electrical-contact pad, the can characterized by a form factor having a perimeter edge defining a boundary of the can, and a recessed portion with an upper surface positioned to lie beneath the bone table when the can is placed in the hole, and that supports the electrical-contact pad;

a cover assembly having a plurality of ports, each of the plurality of ports configured to receive a connector end of a lead, the cover assembly configured to couple to the can and decouple from the can at the electrical-contact pad; and a strain relief system comprising:

a lower strain relief defining a plurality of channels, wherein each of the plurality of channels is configured to receive a portion of a lead body and includes a curved portion that extends upward from a proximal end at or near the upper surface of the recessed portion to a distal end at the bone table, and an upper strain relief configured to cover the plurality of channels of the lower strain relief, wherein the lower strain relief is configured to one of:

couple to the cover assembly and decouple from the cover assembly, or couple to the upper surface of the recessed portion and decouple from the upper surface of the recessed portion of the can.

8. The implantable medical device of claim 7, wherein the lower strain relief further comprises a generally linear portion that extends from the distal end of the curved portion to a terminating end beyond the perimeter edge of the can.

9. The implantable medical device of claim 7, wherein upper strain relief is configured to mechanically couple to and mechanically decouple from the cover assembly.

10. The implantable medical device of claim 7, wherein upper strain relief is configured to mechanically couple to and mechanically decouple from the lower strain relief.

11. The implantable medical device of claim 7, wherein upper strain relief is configured to mechanically couple to and mechanically decouple from both of the cover assembly and the lower strain relief.

12. An implantable medical device configured for implant in a hole in cranium of a patient, relative to a bone table corresponding to a surface of the cranium adjacent the hole, the implantable medical device comprising:

a can having an electrical-contact pad, the can characterized by a form factor having a perimeter edge defining a boundary of the can, and a recessed portion with an upper surface positioned to lie beneath the bone table when the can is placed in the hole, and that supports the electrical-contact pad;

a cover assembly having a plurality of ports, each of the plurality of ports configured to receive a connector end of a lead, the cover assembly configured to couple to the can and decouple from the can at the electrical-contact pad; and a strain relief system comprising:

a lower strain relief defining a plurality of channels, wherein each of the plurality of channels is configured to receive a portion of a lead body and includes a curved portion that extends upward from a proximal end at or near the upper surface of the recessed portion to a distal end at the bone table, and an upper strain relief configured to mechanically couple to a plurality of leads, and to mechanically couple to and decouple from one or both of the cover assembly and the lower strain relief.

13. The implantable medical device of claim 12, wherein the upper strain relief covers the plurality of channels of the lower strain relief.

14. The implantable medical device of claim 12, wherein the upper strain relief comprises a sheath.

15. The implantable medical device of claim 12, wherein the lower strain relief further comprises a generally linear portion that extends from the distal end of the curved portion to a terminating end beyond the perimeter edge of the can.

16. The implantable medical device of claim 12, wherein the upper strain relief includes a curved portion that extends upward from a proximal end to a distal end, and a generally linear portion that extends from the distal end of the curved portion.

* * * * *